United States Patent
Yang et al.

(10) Patent No.: US 12,173,020 B2
(45) Date of Patent: Dec. 24, 2024

(54) NEW-TYPE OXAZOLIDINONE COMPOUNDS AND PREPARATION METHOD THEREFOR

(71) Applicant: HC SYNTHETIC PHARMACEUTICAL CO., LTD., Xi'an (CN)

(72) Inventors: Cheng Yang, Xi'an (CN); Dongxing Li, Xi'an (CN); Sumin Qi, Xi'an (CN); Qiyuan Zhang, Xi'an (CN); Tieshan Chen, Xi'an (CN); Xiaodan Zhao, Xi'an (CN)

(73) Assignee: HC SYNTHETIC PHARMACEUTICAL CO., LTD., Shaanxi Province (CN)

( * ) Notice: Subject to any disclaimer, the term of this patent is extended or adjusted under 35 U.S.C. 154(b) by 249 days.

(21) Appl. No.: 17/783,003

(22) PCT Filed: Jul. 1, 2020

(86) PCT No.: PCT/CN2020/099663
§ 371 (c)(1),
(2) Date: Jun. 7, 2022

(87) PCT Pub. No.: WO2021/114639
PCT Pub. Date: Jun. 17, 2021

(65) Prior Publication Data
US 2023/0046407 A1     Feb. 16, 2023

(30) Foreign Application Priority Data

Dec. 11, 2019   (CN) .......................... 201911270803.8

(51) Int. Cl.
*A61P 31/04*   (2006.01)
*C07F 9/6558*   (2006.01)

(52) U.S. Cl.
CPC .......... *C07F 9/65583* (2013.01); *A61P 31/04* (2018.01)

(58) Field of Classification Search
CPC ............................. C07F 9/65583; A61P 31/04
USPC ............................................................ 514/89
See application file for complete search history.

(56) References Cited

FOREIGN PATENT DOCUMENTS

| CN | 1894242 | A |   | 1/2007 |
|----|---------|---|---|--------|
| CN | 101720325 | A |   | 6/2010 |
| CN | 105085570 | A | * | 11/2015 |
| CN | 106146558 | A |   | 11/2016 |
| CN | 107400126 | A |   | 11/2017 |
| JP | 2004521147 | A |   | 7/2004 |
| JP | 2007514737 | A |   | 8/2011 |
| JP | 2010535768 | A1 |   | 3/2014 |
| WO | WO2016/088102 | A1 |   | 6/2016 |
| WO | 2017181948 | A1 |   | 10/2017 |

OTHER PUBLICATIONS

ISR for PCT/CN2020/099663, Jul. 1, 2020.
Im, Weon Bin et al. "Discovery of torezolid as a novel 5-hydroxymethyl-oxazolidinone antibacterial agent", European Journal of Medicinal Chemistry, vol. 46, No. 4, (Jan. 18, 2011), pp. 1027-1039.

* cited by examiner

*Primary Examiner* — Kahsay Habte
(74) *Attorney, Agent, or Firm* — AKC PATENTS, LLC; Aliki K. Collins

(57) ABSTRACT

Oxazolidinones having structures represented by structural formula I, preparation methods therefor, and pharmaceutical uses thereof, in particular an application of said compounds and salts or compositions thereof in the treatment of a bacterial infection. In the formula: $R^1$ is a methyl group, an ethyl group, a propyl group, a cyclopropyl group, or a vinyl group; $R^2$ is F; and $R^3$ is F, $CH_3$, $C_2H_5$, $CF_3$, $CHF_2$, $CH_2F$, or a cyclopropyl group.

8 Claims, No Drawings

NEW-TYPE OXAZOLIDINONE COMPOUNDS AND PREPARATION METHOD THEREFOR

CROSS REFERENCE TO RELATED APPLICATION

This disclosure claims the priority of Chinese patent application No. 201911270803.8 entitled New-type Oxazolidinone Compounds and Preparation Method Therefor filed with China National Intellectual Property Administration on Dec. 11, 2019, which is incorporated herein by reference in its entirety.

TECHNICAL FIELD

The present disclosure belongs to the field of medicinal chemistry, and relates to oxazolidinone derivatives with anti-infection activity, to a method for preparing the derivatives and to their use as pharmaceutical drugs.

formula I wherein $R^1$ is methyl, ethyl, propyl, cyclopropyl, or vinyl; $R^2$ is F; $R^3$ is F, $CH_3$, $C_2H_5$, $CF_3$, $CHF_2$, $CH_2F$, or cyclopropyl.

BACKGROUND

A variety of oxazolidinone derivatives have been used as antibacterial drugs and tedizolid is one of these drugs with desirable antibacterial effect. In order to develop oxazolidinone compounds having stronger antibacterial effect, a series of compounds are synthesized by using the tedizolid structure as a guide compound in the present disclosure.

Antibacterial experiments preliminarily show that these newly invented compounds have stronger antibacterial effects than tedizolid.

SUMMARY

The structure of tedizolid has a structure shown in the following formula III:

formula III

Its phosphate ester has better effect in the treatment of acute bacterial skin and skin structure infections (ABSSSI) caused by *Staphylococcus aureus* (including methicillin-resistant strains, methicillin-sensitive strains) and various *Streptococcus* species and Gram-positive bacteria such as *Enterococcus faecalis*.

In order to find a drug having better therapeutic effect, the structure of formula III is properly modified to obtain a series of new compounds in the present disclosure. The modification is conducted by replacing the methyl group linked to the tetrazole ring with ethyl, propyl, cyclopropyl, or vinyl; and/or modifying the hydroxymethyl group at the 5-position of oxazolidinone with fluorine, methyl, ethyl, trifluoromethyl, difluoromethyl, fluoromethyl, or cyclopropyl to introduce a second chiral center. The obtained compound is shown as formula II.

formula II wherein $R^1$ is methyl, ethyl, propyl, cyclopropyl, or vinyl; $R^2$ is F; $R^3$ is F, $CH_3$, $C_2H_5$, $CF_3$, $CHF_2$, $CH_2F$, or cyclopropyl.

Specifically, this series of new compounds includes but is not limited to the following compounds:

(R)-3-(3-fluoro-4-(6-(2-ethyl-2H-tetrazol-5-yl) pyridin-3-yl) phenyl)-5-(hydroxymethyl) oxazolidin-2-one (referred to as compound 1)

(S)-3-(3-fluoro-4-(6-(2-ethyl-2H-tetrazol-5-yl) pyridin-3-yl) phenyl)-5-(hydroxymethyl) oxazolidin-2-one (referred to as compound 2)

(R)-3-(3-fluoro-4-(6-(2-propyl-2H-tetrazol-5-yl) pyridin-3-yl) phenyl)-5-(hydroxymethyl) oxazolidin-2-one (referred to as compound 3)

(S)-3-(3-fluoro-4-(6-(2-propyl-2H-tetrazol-5-yl) pyridin-3-yl) phenyl)-5-(hydroxymethyl) oxazolidin-2-one (referred to as compound 4)

(R)-3-(3-fluoro-4-(6-(2-cyclopropyl-2H-tetrazol-5-yl) pyridin-3-yl) phenyl)-5-(hydroxymethyl) oxazolidin-2-one (referred to as compound 5)

(S)-3-(3-fluoro-4-(6-(2-cyclopropyl-2H-tetrazol-5-yl) pyridin-3-yl) phenyl)-5-(hydroxymethyl) oxazolidin-2-one (referred to as compound 6)

(R)-3-(3-fluoro-4-(6-(2-vinyl-2H-tetrazol-5-yl) pyridin-3-yl) phenyl)-5-(hydroxymethyl) oxazolidin-2-one (referred to as compound 7)

(S)-3-(3-fluoro-4-(6-(2-vinyl-2H-tetrazol-5-yl) pyridin-3-yl) phenyl)-5-(hydroxymethyl) oxazolidin-2-one (referred to as compound 8)

(R)-3-(3-fluoro-4-(6-(2-methyl-2H-tetrazol-5-yl) pyridin-3-yl) phenyl)-5-(1-hydroxyethyl) oxazolidin-2-one (referred to as compound 9)

(S)-3-(3-fluoro-4-(6-(2-methyl-2H-tetrazol-5-yl) pyridin-3-yl) phenyl)-5-(1-hydroxyethyl) oxazolidin-2-one (referred to as compound 10)

(R)-3-(3-fluoro-4-(6-(2-methyl-2H-tetrazol-5-yl) pyridin-3-yl) phenyl)-5-(1-hydroxypropyl) oxazolidin-2-one (referred to as compound 11)

(S)-3-(3-fluoro-4-(6-(2-methyl-2H-tetrazol-5-yl) pyridin-3-yl) phenyl)-5-(1-hydroxypropyl) oxazolidin-2-one (referred to as compound 12)

(R)-3-(3-fluoro-4-(6-(2-methyl-2H-tetrazol-5-yl) pyridin-3-yl) phenyl)-5-(hydroxyfluoromethyl) oxazolidin-2-one (referred to as compound 13)

(S)-3-(3-fluoro-4-(6-(2-methyl-2H-tetrazol-5-yl) pyridin-3-yl) phenyl)-5-(hydroxyfluoromethyl) oxazolidin-2-one (referred to as compound 14)

(R)-3-(3-fluoro-4-(6-(2-methyl-2H-tetrazol-5-yl) pyridin-3-yl) phenyl)-5-(1-hydroxy-2-trifluoroethyl) oxazolidin-2-one (referred to as compound 15)

(S)-3-(3-fluoro-4-(6-(2-methyl-2H-tetrazol-5-yl) pyridin-3-yl) phenyl)-5-(1-hydroxy-2-trifluoroethyl) oxazolidin-2-one (referred to as compound 16)

(R)-3-(3-fluoro-4-(6-(2-ethyl-2H-tetrazol-5-yl) pyridin-3-yl) phenyl)-5-(1-hydroxy-2-trifluoroethyl) oxazolidin-2-one (referred to as compound 17)

(S)-3-(3-fluoro-4-(6-(2-ethyl-2H-tetrazol-5-yl) pyridin-3-yl) phenyl)-5-(1-hydroxy-2-trifluoroethyl) oxazolidin-2-one (referred to as compound 18)

(R)-3-(3-fluoro-4-(6-(2-ethyl-2H-tetrazol-5-yl) pyridin-3-yl) phenyl)-5-(1-hydroxyethyl) oxazolidin-2-one (referred to as compound 19)

(S)-3-(3-fluoro-4-(6-(2-ethyl-2H-tetrazol-5-yl) pyridin-3-yl) phenyl)-5-(1-hydroxyethyl) oxazolidin-2-one (referred to as compound 20)

(R)-3-(3-fluoro-4-(6-(2-ethyl-2H-tetrazol-5-yl) pyridin-3-yl) phenyl)-5-(1-hydroxypropyl) oxazolidin-2-one (referred to as compound 21)

(S)-3-(3-fluoro-4-(6-(2-ethyl-2H-tetrazol-5-yl) pyridin-3-yl) phenyl)-5-(1-hydroxypropyl) oxazolidin-2-one (referred to as compound 22)

(R)-3-(3-fluoro-4-(6-(2-ethyl-2H-tetrazol-5-yl) pyridin-3-yl) phenyl)-5-(hydroxyfluoromethyl) oxazolidin-2-one (referred to as compound 23)

(S)-3-(3-fluoro-4-(6-(2-ethyl-2H-tetrazol-5-yl) pyridin-3-yl) phenyl)-5-(hydroxyfluoromethyl) oxazolidin-2-one (referred to as compound 24)

(R)-3-(3-fluoro-4-(6-(2-propyl-2H-tetrazol-5-yl) pyridin-3-yl) phenyl)-5-(1-hydroxy-2-trifluoroethyl) oxazolidin-2-one (referred to as compound 25)

(S)-3-(3-fluoro-4-(6-(2-propyl-2H-tetrazol-5-yl) pyridin-3-yl) phenyl)-5-(1-hydroxy-2-trifluoroethyl) oxazolidin-2-one (referred to as compound 26)

(R)-3-(3-fluoro-4-(6-(2-propyl-2H-tetrazol-5-yl) pyridin-3-yl) phenyl)-5-(1-hydroxyethyl) oxazolidin-2-one (referred to as compound 27)

(S)-3-(3-fluoro-4-(6-(2-propyl-2H-tetrazol-5-yl) pyridin-3-yl) phenyl)-5-(1-hydroxyethyl) oxazolidin-2-one (referred to as compound 28)

(R)-3-(3-fluoro-4-(6-(2-propyl-2H-tetrazol-5-yl) pyridin-3-yl) phenyl)-5-(1-hydroxypropyl) oxazolidin-2-one (referred to as compound 29)

(S)-3-(3-fluoro-4-(6-(2-propyl-2H-tetrazol-5-yl) pyridin-3-yl) phenyl)-5-(1-hydroxypropyl) oxazolidin-2-one (referred to as compound 30)

(R)-3-(3-fluoro-4-(6-(2-propyl-2H-tetrazol-5-yl) pyridin-3-yl) phenyl)-5-(hydroxyfluoromethyl) oxazolidin-2-one (referred to as compound 31)

(S)-3-(3-fluoro-4-(6-(2-propyl-2H-tetrazol-5-yl) pyridin-3-yl) phenyl)-5-(hydroxyfluoromethyl) oxazolidin-2-one (referred to as compound 32)

(R)-3-(3-fluoro-4-(6-(2-cyclopropyl-2H-tetrazol-5-yl) pyridin-3-yl) phenyl)-5-(1-hydroxy-2-trifluoroethyl) oxazolidin-2-one (referred to as compound 33)

(S)-3-(3-fluoro-4-(6-(2-cyclopropyl-2H-tetrazol-5-yl) pyridin-3-yl) phenyl)-5-(1-hydroxy-2-trifluoroethyl) oxazolidin-2-one (referred to as compound 34)

(R)-3-(3-fluoro-4-(6-(2-cyclopropyl-2H-tetrazol-5-yl) pyridin-3-yl) phenyl)-5-(1-hydroxyethyl) oxazolidin-2-one (referred to as compound 35)

(S)-3-(3-fluoro-4-(6-(2-cyclopropyl-2H-tetrazol-5-yl) pyridin-3-yl) phenyl)-5-(1-hydroxyethyl) oxazolidin-2-one (referred to as compound 36)

(R)-3-(3-fluoro-4-(6-(2-cyclopropyl-2H-tetrazol-5-yl) pyridin-3-yl) phenyl)-5-(1-hydroxypropyl)) oxazolidin-2-one (referred to as compound 37)

(S)-3-(3-fluoro-4-(6-(2-cyclopropyl-2H-tetrazol-5-yl) pyridin-3-yl) phenyl)-5-(1-hydroxypropyl)) oxazolidin-2-one (referred to as compound 38)

(R)-3-(3-fluoro-4-(6-(2-cyclopropyl-2H-tetrazol-5-yl) pyridin-3-yl) phenyl)-5-(hydroxyfluoromethyl)) oxazolidin-2-one (referred to as compound 39)

(S)-3-(3-fluoro-4-(6-(2-cyclopropyl-2H-tetrazol-5-yl) pyridin-3-yl) phenyl)-5-(hydroxyfluoromethyl)) oxazolidin-2-one (referred to as compound 40)

(R)-3-(3-fluoro-4-(6-(2-vinyl-2H-tetrazol-5-yl) pyridin-3-yl) phenyl)-5-(1-hydroxy-2-trifluoroethyl) oxazolidin-2-one (referred to as compound 41)

(S)-3-(3-fluoro-4-(6-(2-vinyl-2H-tetrazol-5-yl) pyridin-3-yl) phenyl)-5-(1-hydroxy-2-trifluoroethyl) oxazolidin-2-one (referred to as compound 42)

(R)-3-(3-fluoro-4-(6-(2-vinyl-2H-tetrazol-5-yl) pyridin-3-yl) phenyl)-5-(1-hydroxyethyl) oxazolidin-2-one (referred to as compound 43)

(S)-3-(3-fluoro-4-(6-(2-vinyl-2H-tetrazol-5-yl) pyridin-3-yl) phenyl)-5-(1-hydroxyethyl) oxazolidin-2-one (referred to as compound 44)

(R)-3-(3-fluoro-4-(6-(2-vinyl-2H-tetrazol-5-yl) pyridin-3-yl) phenyl)-5-(1-hydroxypropyl) oxazolidin-2-one (referred to as compound 45)

(S)-3-(3-fluoro-4-(6-(2-vinyl-2H-tetrazol-5-yl) pyridin-3-yl) phenyl)-5-(1-hydroxypropyl) oxazolidin-2-one (referred to as compound 46)

(R)-3-(3-fluoro-4-(6-(2-vinyl-2H-tetrazol-5-yl) pyridin-3-yl) phenyl)-5-(hydroxy fluoromethyl) oxazolidin-2-one (referred to as compound 47)

(S)-3-(3-fluoro-4-(6-(2-vinyl-2H-tetrazol-5-yl) pyridin-3-yl) phenyl)-5-(hydroxy fluoromethyl) oxazolidin-2-one (referred to as compound 48)

(R)-3-(3-fluoro-4-(6-(2-methyl-2H-tetrazol-5-yl) pyridin-3-yl) phenyl)-5-(1-hydroxy-2-difluoroethyl) oxazolidin-2-one (referred to as compound 49)

(S)-3-(3-fluoro-4-(6-(2-methyl-2H-tetrazol-5-yl) pyridin-3-yl) phenyl)-5-(1-hydroxy-2-difluoroethyl) oxazolidin-2-one (referred to as compound 50)

(R)-3-(3-fluoro-4-(6-(2-methyl-2H-tetrazol-5-yl) pyridin-3-yl) phenyl)-5-(1-hydroxy-2-fluoroethyl) oxazolidin-2-one (referred to as compound 51)

(S)-3-(3-fluoro-4-(6-(2-methyl-2H-tetrazol-5-yl) pyridin-3-yl) phenyl)-5-(1-hydroxy-2-fluoroethyl) oxazolidin-2-one (referred to as compound 52)

(R)-3-(3-fluoro-4-(6-(2-methyl-2H-tetrazol-5-yl) pyridin-3-yl) phenyl)-5-(1-hydroxy-1-cyclopropylmethyl) oxazolidin-2-one (referred to as compound 53)

(S)-3-(3-fluoro-4-(6-(2-methyl-2H-tetrazol-5-yl) pyridin-3-yl) phenyl)-5-(1-hydroxy-1-cyclopropylmethyl) oxazolidin-2-one (referred to as compound 54)

(R)-3-(3-fluoro-4-(6-(2-ethyl-2H-tetrazol-5-yl) pyridin-3-yl) phenyl)-5-(1-hydroxy-2-difluoroethyl) oxazolidin-2-one (referred to as compound 55)

(S)-3-(3-fluoro-4-(6-(2-ethyl-2H-tetrazol-5-yl) pyridin-3-yl) phenyl)-5-(1-hydroxy-2-difluoroethyl) oxazolidin-2-one (referred to as compound 56)

(R)-3-(3-fluoro-4-(6-(2-ethyl-2H-tetrazol-5-yl) pyridin-3-yl) phenyl)-5-(1-hydroxy-2-fluoroethyl) oxazolidin-2-one (referred to as compound 57)

(S)-3-(3-fluoro-4-(6-(2-ethyl-2H-tetrazol-5-yl) pyridin-3-yl) phenyl)-5-(1-hydroxy-2-fluoroethyl) oxazolidin-2-one (referred to as compound 58)

(R)-3-(3-fluoro-4-(6-(2-ethyl-2H-tetrazol-5-yl) pyridin-3-yl) phenyl)-5-(1-hydroxy-1-cyclopropylmethyl) oxazolidin-2-one (referred to as compound 59)

(S)-3-(3-fluoro-4-(6-(2-ethyl-2H-tetrazol-5-yl) pyridin-3-yl) phenyl)-5-(1-hydroxy-1-cyclopropylmethyl) oxazolidin-2-one (referred to as compound 60)

(R)-3-(3-fluoro-4-(6-(2-propyl-2H-tetrazol-5-yl) pyridin-3-yl) phenyl)-5-(1-hydroxy-2-difluoroethyl) oxazolidin-2-one (referred to as compound 61)

(S)-3-(3-fluoro-4-(6-(2-propyl-2H-tetrazol-5-yl) pyridin-3-yl) phenyl)-5-(1-hydroxy-2-difluoroethyl) oxazolidin-2-one (referred to as compound 62)

(R)-3-(3-fluoro-4-(6-(2-propyl-2H-tetrazol-5-yl) pyridin-3-yl) phenyl)-5-(1-hydroxy-2-fluoroethyl) oxazolidin-2-one (referred to as compound 63)

(S)-3-(3-fluoro-4-(6-(2-propyl-2H-tetrazol-5-yl) pyridin-3-yl) phenyl)-5-(1-hydroxy-2-fluoroethyl) oxazolidin-2-one (referred to as compound 64)

(R)-3-(3-fluoro-4-(6-(2-propyl-2H-tetrazol-5-yl) pyridin-3-yl) phenyl)-5-(1-hydroxy-1-cyclopropylmethyl) oxazolidin-2-one (referred to as compound 65)

(S)-3-(3-fluoro-4-(6-(2-propyl-2H-tetrazol-5-yl) pyridin-3-yl) phenyl)-5-(1-hydroxy-1-cyclopropylmethyl) oxazolidin-2-one (referred to as compound 66)

(R)-3-(3-fluoro-4-(6-(2-cyclopropyl-2H-tetrazol-5-yl) pyridin-3-yl) phenyl)-5-(1-hydroxy-2-difluoroethyl) oxazolidin-2-one (referred to as compound 67)

(S)-3-(3-fluoro-4-(6-(2-cyclopropyl-2H-tetrazol-5-yl) pyridin-3-yl) phenyl)-5-(1-hydroxy-2-difluoroethyl) oxazolidin-2-one (referred to as compound 68)

(R)-3-(3-fluoro-4-(6-(2-cyclopropyl-2H-tetrazol-5-yl) pyridin-3-yl) phenyl)-5-(1-hydroxy-2-fluoroethyl) oxazolidin-2-one (referred to as compound 69)

(S)-3-(3-fluoro-4-(6-(2-cyclopropyl-2H-tetrazol-5-yl) pyridin-3-yl) phenyl)-5-(1-hydroxy-2-fluoroethyl) oxazolidin-2-one (referred to as compound 70)

(R)-3-(3-fluoro-4-(6-(2-cyclopropyl-2H-tetrazol-5-yl) pyridin-3-yl) phenyl)-5-(1-hydroxy-1-cyclopropylmethyl) oxazolidin-2-one (referred to as compound 71)

(S)-3-(3-fluoro-4-(6-(2-cyclopropyl-2H-tetrazol-5-yl) pyridin-3-yl) phenyl)-5-(1-hydroxy-1-cyclopropylmethyl) oxazolidin-2-one (referred to as compound 72)

(R)-3-(3-fluoro-4-(6-(2-vinyl-2H-tetrazol-5-yl) pyridin-3-yl) phenyl)-5-(1-hydroxy-2-difluoroethyl) oxazolidin-2-one (referred to as compound 73)

(S)-3-(3-fluoro-4-(6-(2-vinyl-2H-tetrazol-5-yl) pyridin-3-yl) phenyl)-5-(1-hydroxy-2-difluoroethyl) oxazolidin-2-one (referred to as compound 74)

(R)-3-(3-fluoro-4-(6-(2-vinyl-2H-tetrazol-5-yl) pyridin-3-yl) phenyl)-5-(1-hydroxy-2-fluoroethyl) oxazolidin-2-one (referred to as compound 75)

(S)-3-(3-fluoro-4-(6-(2-vinyl-2H-tetrazol-5-yl) pyridin-3-yl) phenyl)-5-(1-hydroxy-2-fluoroethyl) oxazolidin-2-one (referred to as compound 76)

(R)-3-(3-fluoro-4-(6-(2-vinyl-2H-tetrazol-5-yl) pyridin-3-yl) phenyl)-5-(1-hydroxy-1-cyclopropylmethyl) oxazolidin-2-one (referred to as compound 77)

(S)-3-(3-fluoro-4-(6-(2-vinyl-2H-tetrazol-5-yl) pyridin-3-yl) phenyl)-5-(1-hydroxy-1-cyclopropylmethyl) oxazolidin-2-one (referred to as compound 78).

To obtain the compound of formula II, a compound of formula IV and a compound of formula V are coupled.

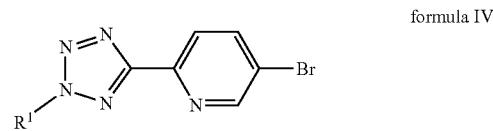

formula IV wherein $R^1$ is methyl, ethyl, propyl, cyclopropyl, or vinyl;

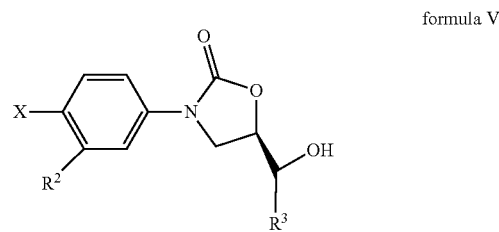

formula V wherein $R^2$ is F; $R^3$ is F, $CH_3$, $C_2H_5$, $CF_3$, $CHF_2$, $CH_2F$ or cyclopropyl; X is chlorine (Cl), bromine (Br), iodine (I), substituted boronic acid or substituted boronic acid ester.

Specifically, the compound of formula IV and the compound of formula V are coupled under the action of a catalyst. Alternatively, one of the compounds of formula IV and the compound formula V is made into a Grignard reagent, and then coupled with an additional corresponding moiety. The following catalysts may be used: copper iodide, bis(triphenylphosphine) palladium chloride, palladium chloride, palladium acetate, bis(tri-tert-butylphosphine) palladium chloride, 1,1'-bis (di-tert-butylphosphine) ferrocene palladium dichloride, bis (diphenylphosphino) ferrocene palladium dichloride, (1,1'-bis (diphenylphosphino) ferrocene) nickel dichloride, tris(triphenylphosphine) ruthenium chloride, bis (acetonitrile) palladium (II) chloride, 1,4-bis (diphenylphosphinobutane) palladium chloride, bis (di-tert-butylphenylphosphine) palladium (II) chloride, bis (triphenylphosphine) palladium acetate, 1,1'-bis (diphenylphosphino) ferrocene palladium (II) dichloride, bis ((4-dimethylaminophenyl)-di-tert-butylphosphine) palladium (II) dichloride. Bis (diphenylphosphino) ferrocene palladium dichloride is preferred.

Compound of formula IV and compound of formula V can be obtained using common organic synthesis methods.

Compound of formula I are obtained by phosphorylation of compound of formula II:

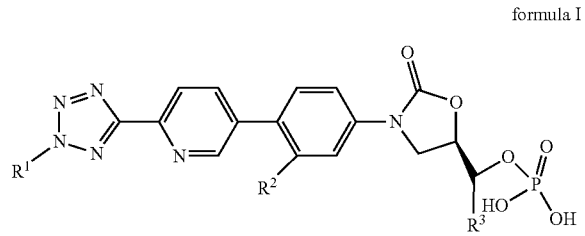

formula I wherein $R^1$ is methyl, ethyl, propyl, cyclopropyl, or vinyl; $R^2$ is F; $R^3$ is F, $CH_3$, $C_2H_5$, $CF_3$, $CHF_2$, $CH_2F$, or cyclopropyl. This series of compounds specifically includes but is not limited to the following compounds:

(R)-3-(3-fluoro-4-(6-(2-ethyl-2H-tetrazol-5-yl) pyridin-3-yl) phenyl)-5-(hydroxymethyl) oxazolidin-2-one phosphate (referred to as compound 79)

(S)-3-(3-fluoro-4-(6-(2-ethyl-2H-tetrazol-5-yl) pyridin-3-yl) phenyl)-5-(hydroxymethyl) oxazolidin-2-one phosphate (referred to as compound 80)

(R)-3-(3-fluoro-4-(6-(2-propyl-2H-tetrazol-5-yl) pyridin-3-yl) phenyl)-5-(hydroxymethyl) oxazolidin-2-one phosphate (referred to as compound 81)

(S)-3-(3-fluoro-4-(6-(2-propyl-2H-tetrazol-5-yl) pyridin-3-yl) phenyl)-5-(hydroxymethyl) oxazolidin-2-one phosphate (referred to as compound 82)

(R)-3-(3-fluoro-4-(6-(2-cyclopropyl-2H-tetrazol-5-yl) pyridin-3-yl) phenyl)-5-(hydroxymethyl) oxazolidin-2-one phosphate (referred to as compound 83)

(S)-3-(3-fluoro-4-(6-(2-cyclopropyl-2H-tetrazol-5-yl) pyridin-3-yl) phenyl)-5-(hydroxymethyl) oxazolidin-2-one phosphate (referred to as compound 84)

(R)-3-(3-fluoro-4-(6-(2-vinyl-2H-tetrazol-5-yl) pyridin-3-yl) phenyl)-5-(hydroxymethyl) oxazolidin-2-one phosphate (referred to as compound 85)

(S)-3-(3-fluoro-4-(6-(2-vinyl-2H-tetrazol-5-yl) pyridin-3-yl) phenyl)-5-(hydroxymethyl) oxazolidin-2-one phosphate (referred to as compound 86)

(R)-3-(3-fluoro-4-(6-(2-methyl-2H-tetrazol-5-yl) pyridin-3-yl) phenyl)-5-(1-hydroxyethyl) oxazolidin-2-one phosphate (referred to as compound 87)

(S)-3-(3-fluoro-4-(6-(2-methyl-2H-tetrazol-5-yl) pyridin-3-yl) phenyl)-5-(1-hydroxyethyl) oxazolidin-2-one phosphate (referred to as compound 88)

(R)-3-(3-fluoro-4-(6-(2-methyl-2H-tetrazol-5-yl) pyridin-3-yl) phenyl)-5-(1-hydroxypropyl) oxazolidin-2-one phosphate (referred to as compound 89)

(S)-3-(3-fluoro-4-(6-(2-methyl-2H-tetrazol-5-yl) pyridin-3-yl) phenyl)-5-(1-hydroxypropyl) oxazolidin-2-one phosphate (referred to as compound 90)

(R)-3-(3-fluoro-4-(6-(2-methyl-2H-tetrazol-5-yl) pyridin-3-yl) phenyl)-5-(hydroxyfluoromethyl) oxazolidin-2-one phosphate (referred to as compound 91)

(S)-3-(3-fluoro-4-(6-(2-methyl-2H-tetrazol-5-yl) pyridin-3-yl) phenyl)-5-(hydroxyfluoromethyl) oxazolidin-2-one phosphate (referred to as compound 92)

(R)-3-(3-fluoro-4-(6-(2-methyl-2H-tetrazol-5-yl) pyridin-3-yl) phenyl)-5-(1-hydroxy-2-trifluoroethyl) oxazolidin-2-one phosphate (referred to as compound 93)

(S)-3-(3-fluoro-4-(6-(2-methyl-2H-tetrazol-5-yl) pyridin-3-yl) phenyl)-5-(1-hydroxy-2-trifluoroethyl) oxazolidin-2-one phosphate (referred to as compound 94)

(R)-3-(3-fluoro-4-(6-(2-ethyl-2H-tetrazol-5-yl) pyridin-3-yl) phenyl)-5-(1-hydroxy-2-trifluoroethyl) oxazolidin-2-one phosphate (referred to as compound 95)

(S)-3-(3-fluoro-4-(6-(2-ethyl-2H-tetrazol-5-yl) pyridin-3-yl) phenyl)-5-(1-hydroxy-2-trifluoroethyl) oxazolidin-2-one phosphate (referred to as compound 96)

(R)-3-(3-fluoro-4-(6-(2-ethyl-2H-tetrazol-5-yl) pyridin-3-yl) phenyl)-5-(1-hydroxyethyl) oxazolidin-2-one phosphate (referred to as compound 97)

(S)-3-(3-fluoro-4-(6-(2-ethyl-2H-tetrazol-5-yl) pyridin-3-yl) phenyl)-5-(1-hydroxyethyl) oxazolidin-2-one phosphate (referred to as compound 98)

(R)-3-(3-fluoro-4-(6-(2-ethyl-2H-tetrazol-5-yl) pyridin-3-yl) phenyl)-5-(1-hydroxypropyl) oxazolidin-2-one phosphate (referred to as compound 99)

(S)-3-(3-fluoro-4-(6-(2-ethyl-2H-tetrazol-5-yl) pyridin-3-yl) phenyl)-5-(1-hydroxypropyl) oxazolidin-2-one phosphate (referred to as compound 100)

(R)-3-(3-fluoro-4-(6-(2-ethyl-2H-tetrazol-5-yl) pyridin-3-yl) phenyl)-5-(hydroxyfluoromethyl) oxazolidin-2-one phosphate (referred to as compound 101)

(S)-3-(3-fluoro-4-(6-(2-ethyl-2H-tetrazol-5-yl) pyridin-3-yl) phenyl)-5-(hydroxyfluoromethyl) oxazolidin-2-one phosphate (referred to as compound 102)

(R)-3-(3-fluoro-4-(6-(2-propyl-2H-tetrazol-5-yl) pyridin-3-yl) phenyl)-5-(1-hydroxy-2-trifluoroethyl) oxazolidin-2-one phosphate (referred to as compound 103)

(S)-3-(3-fluoro-4-(6-(2-propyl-2H-tetrazol-5-yl) pyridin-3-yl) phenyl)-5-(1-hydroxy-2-trifluoroethyl) oxazolidin-2-one phosphate (referred to as compound 104)

(R)-3-(3-fluoro-4-(6-(2-propyl-2H-tetrazol-5-yl) pyridin-3-yl) phenyl)-5-(1-hydroxyethyl) oxazolidin-2-one phosphate (referred to as compound 105)

(S)-3-(3-fluoro-4-(6-(2-propyl-2H-tetrazol-5-yl) pyridin-3-yl) phenyl)-5-(1-hydroxyethyl) oxazolidin-2-one phosphate (referred to as compound 106)

(R)-3-(3-fluoro-4-(6-(2-propyl-2H-tetrazol-5-yl) pyridin-3-yl) phenyl)-5-(1-hydroxypropyl) oxazolidin-2-one phosphate (referred to as compound 107)

(S)-3-(3-fluoro-4-(6-(2-propyl-2H-tetrazol-5-yl) pyridin-3-yl) phenyl)-5-(1-hydroxypropyl) oxazolidin-2-one phosphate (referred to as compound 108)

(R)-3-(3-fluoro-4-(6-(2-propyl-2H-tetrazol-5-yl) pyridin-3-yl) phenyl)-5-(hydroxyfluoromethyl) oxazolidin-2-one phosphate (referred to as compound 109)

(S)-3-(3-fluoro-4-(6-(2-propyl-2H-tetrazol-5-yl) pyridin-3-yl) phenyl)-5-(hydroxyfluoromethyl) oxazolidin-2-one phosphate (referred to as compound 110)

(R)-3-(3-fluoro-4-(6-(2-cyclopropyl-2H-tetrazol-5-yl) pyridin-3-yl) phenyl)-5-(1-hydroxy-2-trifluoroethyl) oxazolidin-2-one phosphate (referred to as compound 111)

(S)-3-(3-fluoro-4-(6-(2-cyclopropyl-2H-tetrazol-5-yl) pyridin-3-yl) phenyl)-5-(1-hydroxy-2-trifluoroethyl) oxazolidin-2-one phosphate (referred to as compound 112)

(R)-3-(3-fluoro-4-(6-(2-cyclopropyl-2H-tetrazol-5-yl) pyridin-3-yl) phenyl)-5-(1-hydroxyethyl) oxazolidin-2-one phosphate (referred to as compound 113)

(S)-3-(3-fluoro-4-(6-(2-cyclopropyl-2H-tetrazol-5-yl) pyridin-3-yl) phenyl)-5-(1-hydroxyethyl) oxazolidin-2-one phosphate (referred to as compound 114)

(R)-3-(3-fluoro-4-(6-(2-cyclopropyl-2H-tetrazol-5-yl) pyridin-3-yl) phenyl)-5-(1-hydroxypropyl)) oxazolidin-2-one phosphate (referred to as compound 115)

(S)-3-(3-fluoro-4-(6-(2-cyclopropyl-2H-tetrazol-5-yl) pyridin-3-yl) phenyl)-5-(1-hydroxypropyl)) oxazolidin-2-one phosphate (referred to as compound 116)

(R)-3-(3-fluoro-4-(6-(2-cyclopropyl-2H-tetrazol-5-yl) pyridin-3-yl) phenyl)-5-(hydroxyfluoromethyl)) oxazolidin-2-one phosphate (referred to as compound 117)

(S)-3-(3-fluoro-4-(6-(2-cyclopropyl-2H-tetrazol-5-yl) pyridin-3-yl) phenyl)-5-(hydroxyfluoromethyl)) oxazolidin-2-one phosphate (referred to as compound 118)

(R)-3-(3-fluoro-4-(6-(2-vinyl-2H-tetrazol-5-yl) pyridin-3-yl) phenyl)-5-(1-hydroxy-2-trifluoroethyl) oxazolidin-2-one phosphate (referred to as compound 119)

(S)-3-(3-fluoro-4-(6-(2-vinyl-2H-tetrazol-5-yl) pyridin-3-yl) phenyl)-5-(1-hydroxy-2-trifluoroethyl) oxazolidin-2-one phosphate (referred to as compound 120)

(R)-3-(3-fluoro-4-(6-(2-vinyl-2H-tetrazol-5-yl) pyridin-3-yl) phenyl)-5-(1-hydroxyethyl) oxazolidin-2-one phosphate (referred to as compound 121)

(S)-3-(3-fluoro-4-(6-(2-vinyl-2H-tetrazol-5-yl) pyridin-3-yl) phenyl)-5-(1-hydroxyethyl) oxazolidin-2-one phosphate (referred to as compound 122)

(R)-3-(3-fluoro-4-(6-(2-vinyl-2H-tetrazol-5-yl) pyridin-3-yl) phenyl)-5-(1-hydroxypropyl) oxazolidin-2-one phosphate (referred to as compound 123)

(S)-3-(3-fluoro-4-(6-(2-vinyl-2H-tetrazol-5-yl) pyridin-3-yl) phenyl)-5-(1-hydroxypropyl) oxazolidin-2-one phosphate (referred to as compound 124)

(R)-3-(3-fluoro-4-(6-(2-vinyl-2H-tetrazol-5-yl) pyridin-3-yl) phenyl)-5-(hydroxyfluoromethyl) oxazolidin-2-one phosphate (referred to as compound 125)

(S)-3-(3-fluoro-4-(6-(2-vinyl-2H-tetrazol-5-yl) pyridin-3-yl) phenyl)-5-(hydroxyfluoromethyl) oxazolidin-2-one phosphate (referred to as compound 126)

(R)-3-(3-fluoro-4-(6-(2-methyl-2H-tetrazol-5-yl) pyridin-3-yl) phenyl)-5-(1-hydroxy-2-difluoroethyl) oxazolidin-2-one phosphate (referred to as compound 127)

(S)-3-(3-fluoro-4-(6-(2-methyl-2H-tetrazol-5-yl) pyridin-3-yl) phenyl)-5-(1-hydroxy-2-difluoroethyl) oxazolidin-2-one phosphate (referred to as compound 128)

(R)-3-(3-fluoro-4-(6-(2-methyl-2H-tetrazol-5-yl) pyridin-3-yl) phenyl)-5-(1-hydroxy-2-fluoroethyl) oxazolidin-2-one phosphate (referred to as compound 129)

(S)-3-(3-fluoro-4-(6-(2-methyl-2H-tetrazol-5-yl) pyridin-3-yl) phenyl)-5-(1-hydroxy-2-fluoroethyl) oxazolidin-2-one phosphate (referred to as compound 130)

(R)-3-(3-fluoro-4-(6-(2-methyl-2H-tetrazol-5-yl) pyridin-3-yl) phenyl)-5-(1-hydroxy-1-cyclopropylmethyl) oxazolidin-2-one phosphate (referred to as compound 131)

(S)-3-(3-fluoro-4-(6-(2-methyl-2H-tetrazol-5-yl) pyridin-3-yl) phenyl)-5-(1-hydroxy-1-cyclopropylmethyl) oxazolidin-2-one phosphate (referred to as compound 132)

(R)-3-(3-fluoro-4-(6-(2-ethyl-2H-tetrazol-5-yl) pyridin-3-yl) phenyl)-5-(1-hydroxy-2-difluoroethyl) oxazolidin-2-one phosphate (referred to as compound 133)

(S)-3-(3-fluoro-4-(6-(2-ethyl-2H-tetrazol-5-yl) pyridin-3-yl) phenyl)-5-(1-hydroxy-2-difluoroethyl) oxazolidin-2-one phosphate (referred to as compound 134)

(R)-3-(3-fluoro-4-(6-(2-ethyl-2H-tetrazol-5-yl) pyridin-3-yl) phenyl)-5-(1-hydroxy-2-fluoroethyl) oxazolidin-2-one phosphate (referred to as compound 135)

(S)-3-(3-fluoro-4-(6-(2-ethyl-2H-tetrazol-5-yl) pyridin-3-yl) phenyl)-5-(1-hydroxy-2-fluoroethyl) oxazolidin-2-one phosphate (referred to as compound 136)

(R)-3-(3-fluoro-4-(6-(2-ethyl-2H-tetrazol-5-yl) pyridin-3-yl) phenyl)-5-(1-hydroxy-1-cyclopropylmethyl) oxazolidin-2-one phosphate (referred to as compound 137)

(S)-3-(3-fluoro-4-(6-(2-ethyl-2H-tetrazol-5-yl) pyridin-3-yl) phenyl)-5-(1-hydroxy-1-cyclopropylmethyl) oxazolidin-2-one phosphate (referred to as compound 138)

(R)-3-(3-fluoro-4-(6-(2-propyl-2H-tetrazol-5-yl) pyridin-3-yl) phenyl)-5-(1-hydroxy-2-difluoroethyl) oxazolidin-2-one phosphate (referred to as compound 139)

(S)-3-(3-fluoro-4-(6-(2-propyl-2H-tetrazol-5-yl) pyridin-3-yl) phenyl)-5-(1-hydroxy-2-difluoroethyl) oxazolidin-2-one phosphate (referred to as compound 140)

(R)-3-(3-fluoro-4-(6-(2-propyl-2H-tetrazol-5-yl) pyridin-3-yl) phenyl)-5-(1-hydroxy-2-fluoroethyl) oxazolidin-2-one phosphate (referred to as compound 141)

(S)-3-(3-fluoro-4-(6-(2-propyl-2H-tetrazol-5-yl) pyridin-3-yl) phenyl)-5-(1-hydroxy-2-fluoroethyl) oxazolidin-2-one phosphate (referred to as compound 142)

(R)-3-(3-fluoro-4-(6-(2-propyl-2H-tetrazol-5-yl) pyridin-3-yl) phenyl)-5-(1-hydroxy-1-cyclopropylmethyl) oxazolidin-2-one phosphate (referred to as compound 143)

(S)-3-(3-fluoro-4-(6-(2-propyl-2H-tetrazol-5-yl) pyridin-3-yl) phenyl)-5-(1-hydroxy-1-cyclopropylmethyl) oxazolidin-2-one phosphate (referred to as compound 144)

(R)-3-(3-fluoro-4-(6-(2-cyclopropyl-2H-tetrazol-5-yl) pyridin-3-yl) phenyl)-5-(1-hydroxy-2-difluoroethyl) oxazolidin-2-one phosphate (referred to as compound 145)

(S)-3-(3-fluoro-4-(6-(2-cyclopropyl-2H-tetrazol-5-yl) pyridin-3-yl) phenyl)-5-(1-hydroxy-2-difluoroethyl) oxazolidin-2-one phosphate (referred to as compound 146)

(R)-3-(3-fluoro-4-(6-(2-cyclopropyl-2H-tetrazol-5-yl) pyridin-3-yl) phenyl)-5-(1-hydroxy-2-fluoroethyl) oxazolidin-2-one phosphate (referred to as compound 147)

(S)-3-(3-fluoro-4-(6-(2-cyclopropyl-2H-tetrazol-5-yl) pyridin-3-yl) phenyl)-5-(1-hydroxy-2-fluoroethyl) oxazolidin-2-one phosphate (referred to as compound 148)

(R)-3-(3-fluoro-4-(6-(2-cyclopropyl-2H-tetrazol-5-yl) pyridin-3-yl) phenyl)-5-(1-hydroxy-1-cyclopropylmethyl) oxazolidin-2-one phosphate (referred to as compound 149)

(S)-3-(3-fluoro-4-(6-(2-cyclopropyl-2H-tetrazol-5-yl) pyridin-3-yl) phenyl)-5-(1-hydroxy-1-cyclopropylmethyl) oxazolidin-2-one phosphate (referred to as compound 150)

(R)-3-(3-fluoro-4-(6-(2-vinyl-2H-tetrazol-5-yl) pyridin-3-yl) phenyl)-5-(1-hydroxy-2-difluoroethyl) oxazolidin-2-one phosphate (referred to as compound 151)

(S)-3-(3-fluoro-4-(6-(2-vinyl-2H-tetrazol-5-yl) pyridin-3-yl) phenyl)-5-(1-hydroxy-2-difluoroethyl) oxazolidin-2-one phosphate (referred to as compound 152)

(R)-3-(3-fluoro-4-(6-(2-vinyl-2H-tetrazol-5-yl) pyridin-3-yl) phenyl)-5-(1-hydroxy-2-fluoroethyl) oxazolidin-2-one phosphate (referred to as compound 153)

(S)-3-(3-fluoro-4-(6-(2-vinyl-2H-tetrazol-5-yl) pyridin-3-yl) phenyl)-5-(1-hydroxy-2-fluoroethyl) oxazolidin-2-one phosphate (referred to as compound 154)

(R)-3-(3-fluoro-4-(6-(2-vinyl-2H-tetrazol-5-yl) pyridin-3-yl) phenyl)-5-(1-hydroxy-1-cyclopropylmethyl) oxazolidin-2-one phosphate (referred to as compound 155)

(S)-3-(3-fluoro-4-(6-(2-vinyl-2H-tetrazol-5-yl) pyridin-3-yl) phenyl)-5-(1-hydroxy-1-cyclopropylmethyl) oxazolidin-2-one phosphate (referred to as compound 156)

In order to obtain the compound of formula I, there is a need to react compound of formula II with an halogenated ester of phosphoric acid, and then remove the hydrocarbyl group on the phosphoric acid ester under the action of trimethylbromosilane or trimethylchlorosilane. The halogenated ester of phosphoric acid is selected from the group consisting of dimethyl chlorophosphate, diethyl chlorophosphate, dibenzyl chlorophosphate, dimethyl bromophosphate, diethyl bromophosphate, and dibenzyl bromophosphate. Use of dimethyl chlorophosphate and dimethyl bromophosphate is preferred.

In order to obtain the compound of formula I, it is possible to react the compound of formula II with phosphorus oxychloride or phosphorus oxybromide, and further hydrolyze the reaction product. It is preferred to use phosphorus oxychloride as a reaction starting material.

The process for preparation of such compounds can be expressed by the following scheme:

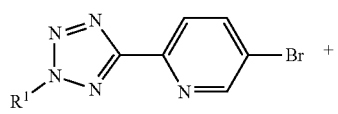

-continued

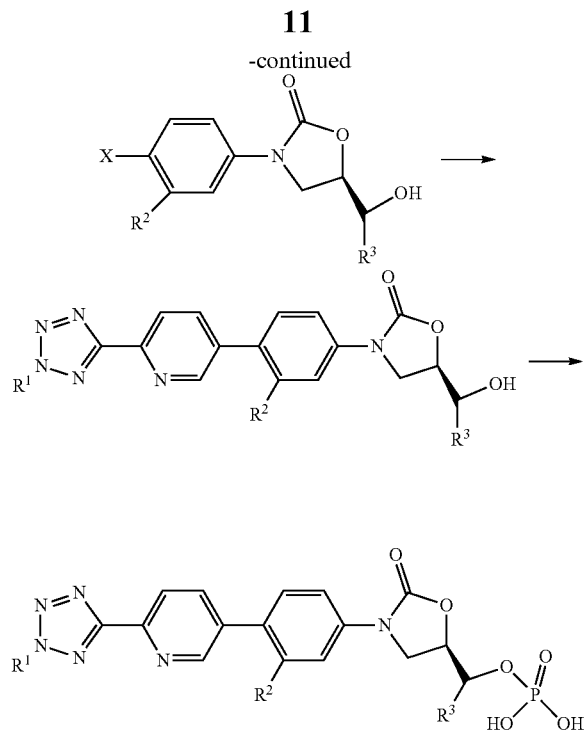

The compounds of the present disclosure or compositions containing the compounds and pharmaceutically acceptable salts thereof can be used for the treatment of bacterial infections in humans or other warm-blooded animals, and the mode of administration may be parenteral or oral. In the present disclosure, antibacterial activity of these new compounds is tested through in vitro antibacterial tests. The results show that, compared with tedizolid, the compound of the present disclosure has stronger antibacterial activity.

DETAILED DESCRIPTION OF THE EMBODIMENTS

In order to better show the essence of the present disclosure and to implement the present disclosure, the following examples are provided. It should be appreciated by those skilled in the art that the embodiments are only for the purpose of exemplifying the process of the present disclosure, without affecting the scope of the present disclosure.

Example 1

Synthesis of Compound 1

One gram of 6-(2-ethyl-2H-tetrazol-5-yl)-3-bromopyridine was dissolved in 10 ml of toluene, then triphenylphosphine palladium chloride was added and the resulting mixture was stirred and warmed to a temperature of 40° C., and 1.2 g of (R)-3-(3-fluoro-4-bromophenyl)-5-(hydroxymethyl) oxazolidin-2-one was added dropwise to react. After completion of the addition, the reaction was held for 4 hours when the temperature was kept at 40-50° C. The reaction was terminated and the reaction mixture was filtered, the solvent was evaporated to dryness, and the residue was recrystallized from ethanol to afford 1.2 g of white solid. The purity detected by HPLC was 98.02%.

Example 2

Synthesis of Compound 2

0.3 g of magnesium scraps was dissolved in 10 ml of anhydrous tetrahydrofuran, and 0.01 g of iodine was added. It could be observed that bubbles began to come out from the reaction solution. The reaction solution was stirred and a solution of 1 g of 6-(2-ethyl-2H-tetrazol-5-yl)-3-bromopyridine in 5 ml of anhydrous tetrahydrofuran was added dropwise. After addition, the resulting mixture was heated and refluxed for 2 hours. Then a solution of 1.2 g of (S)-3-(3-fluoro-4-bromophenyl)-5-(hydroxymethyl) oxazolidin-2-one in 5 ml of anhydrous tetrahydrofuran was added dropwise and the resulting mixture was refluxed for 4 hours. Work-up: 1 ml of water was added and stirred for 10 minutes, filtered, and the filtrate was evaporated to dryness, and the residue was recrystallized from ethanol to afford 1.1 g of white solid. The purity detected by HPLC was 98.11%.

Example 3

Compound 3 was synthesized using a method similar to that in Example 1.

Example 4

Synthesis of Compound 1

In a 250 mL reaction flask were added DMSO (100 mL), (5R)-3-(4-bromo-3-fluorophenyl)-5-hydroxymethyl oxazolidin-2-one (10.00 g, 34.5 mmol), pinacol diboronate (17.52 g, 69.0 mmol), [1,1'-bis (diphenylphosphino) ferrocene dichloropalladium-dichloromethane complex (1.39 g, 1.7 mmol) and potassium acetate (13.54 g, 138.0 mmol), and the resulting mixture was heated to 80° C. under nitrogen protection, and the reaction was carried out for 14 h. Heating was stopped, and the reaction system was cooled to room temperature. 500 mL of water was added, extracted with ethyl acetate (500 mL×3), the organic layers were combined, washed with saturated brine (400 mL×3), and dried over anhydrous sodium sulfate, the organic phase was filtered by suction filtration, concentrated and used directly for the next step of reaction.

The concentrated product from the previous step was added into a 250 mL reaction flask, then 1,4-dioxane (100 mL), 5-bromo-2-(2-methyl-2H tetrazol-5-yl)) pyridine (compound 3) (8.28 g, 34.5 mmol), [1,1'-bis (diphenyiphosphino) ferrocene]dichloropalladium-dichloromethane complex (0.57 g, 0.7 mmol) and cesium carbonate aqueous solution (50 mL, containing 33.72 g cesium carbonate, 103.5 mmol) were added, and the resulting mixture was heated to 70° C. under nitrogen protection. The reaction was performed for 3 hours and ended. Then dichloromethane (100 mL×3) was added for extraction. The separated organic phase was washed with saturated brine (100 mL), dehydrated with anhydrous sodium sulfate, filtered, concentrated in vacuo and purified by column chromatography to afford 10.60 g of compound 1 in a yield of 82.900 and a purity of 98.34% by HPLC.

A series of similar compounds were synthesized by methods similar to the methods described in Example 1, Example 2, and Example 4. The raw materials and products used are listed as follows.

| Product No. | Raw material (tetrazole-pyridine) | Raw material (oxazolidinone) |
|---|---|---|
| 1 | R¹ = ethyl | X = Br, R² = F, R³ = H |
| 3 | R¹ = ethyl | X = Cl, R² = F, R³ = H |
| 5 | R¹ = propyl | X = Br, R² = F, R³ = H |
| 7 | R¹ = cyclopropyl | X = Br, R² = F, R³ = H |
| 9 | R¹ = vinyl | X = Br, R² = F, R³ = methyl |
| 11 | R¹ = methyl | X = Br, R² = F, R³ = ethyl |
| 13 | R¹ = methyl | X = I, R² = F, R³ = F |
| 15 | R¹ = methyl | X = Br, R² = F, R³ = trifluoromethyl |
| 17 | R¹ = ethyl | X = Br, R² = F, R³ = trifluoromethyl |
| 19 | R¹ = ethyl | X = Br, R² = F, R³ = methyl |
| 21 | R¹ = ethyl | X = Br, R² = F, R³ = ethyl |
| 23 | R¹ = ethyl | X = Br, R² = F, R³ = F |
| 25 | R¹ = propyl | X = Br, R² = F, R³ = trifluoromethyl |
| 27 | R¹ = propyl | X = Br, R² = F, R³ = methyl |
| 29 | R¹ = propyl | X = Br, R² = F, R³ = ethyl |
| 31 | R¹ = propyl | X = Br, R² = F, R³ = F |
| 33 | R¹ = cyclopropyl | X = Br, R² = F, R³ = trifluoromethyl |
| 35 | R¹ = cyclopropyl | X = Br, R² = F, R³ = methyl |
| 37 | R¹ = cyclopropyl | X = Br, R² = F, R³ = ethyl |
| 39 | R¹ = cyclopropyl | X = Br, R² = F, R³ = F |
| 41 | R¹ = vinyl | X = Br, R² = F, R³ = trifluoromethyl |
| 43 | R¹ = vinyl | X = Br, R² = F, R³ = methyl |
| 45 | R¹ = vinyl | X = Br, R² = F, R³ = ethyl |
| 47 | R¹ = vinyl | X = Br, R² = F, R³ = F |
| 49 | R¹ = methyl | X = Br, R² = F, R³ = difluoromethyl |
| 51 | R¹ = methyl | X = Br, R² = F, R³ = fluoromethyl |
| 53 | R¹ = methyl | X = Br, R² = F, R³ = fluoromethyl |
| 55 | R¹ = ethyl | X = Br, R² = F, R³ = cyclopropyl |
| 57 | R¹ = ethyl | X = Br, R² = F, R³ = fluoromethyl |
| 59 | R¹ = ethyl | X = Br, R² = F, R³ = cyclopropyl |
| 61 | R¹ = propyl | X = Br, R² = F, R³ = difluoromethyl |
| 63 | R¹ = propyl | X = Br, R² = F, R³ = fluoromethyl |
| 65 | R¹ = propyl | X = Br, R² = F, R³ = cyclopropyl |
| 67 | R¹ = cyclopropyl | X = Br, R² = F, R³ = difluoromethyl |
| 69 | R¹ = cyclopropyl | X = Br, R² = F, R³ = fluoromethyl |
| 71 | R¹ = cyclopropyl | X = Br, R² = F, R³ = cyclopropyl |
| 73 | R¹ = vinyl | X = Br, R² = F, R³ = difluoromethyl |
| 75 | R¹ = vinyl | X = Br, R² = F, R³ = fluoromethyl |
| 77 | R¹ = vinyl | X = Br, R² = F, R³ = cyclopropyl |

A series of similar compounds were synthesized by methods similar to the methods described in Example 1, Example 2, and Example 4. The raw materials and products used are listed as follows.

| Product No. | Raw material (tetrazole-pyridine) | Raw material (oxazolidinone) |
|---|---|---|
| 2 | R¹ = ethyl | X = Br, R² = F, R³ = H |
| 4 | R¹ = ethyl | X = I, R² = F, R³ = H |
| 6 | R¹ = propyl | X = Br, R² = F, R³ = H |
| 8 | R¹ = cyclopropyl | X = Br, R² = F, R³ = H |
| 10 | R¹ = vinyl | X = Br, R² = F, R³ = methyl |
| 12 | R¹ = methyl | X = Br, R² = F, R³ = ethyl |
| 14 | R¹ = methyl | X = Cl, R² = F, R³ = F |
| 16 | R¹ = methyl | X = Br, R² = F, R³ = trifluoromethyl |

-continued

| Product No. | Raw material (tetrazole-pyridine) | Raw material (oxazolidinone) |
|---|---|---|
| 18 | $R^1$ = ethyl | X = Br, $R^2$ = F, $R^3$ = trifluoromethyl |
| 20 | $R^1$ = ethyl | X = Br, $R^2$ = F, $R^3$ = methyl |
| 22 | $R^1$ = ethyl | X = Br, $R^2$ = F, $R^3$ = ethyl |
| 24 | $R^1$ = ethyl | X = Br, $R^2$ = F, $R^3$ = F |
| 26 | $R^1$ = propyl | X = Br, $R^2$ = F, $R^3$ = trifluoromethyl |
| 28 | $R^1$ = propyl | X = I, $R^2$ = F, $R^3$ = methyl |
| 30 | $R^1$ = propyl | X = Br, $R^2$ = F, $R^3$ = ethyl |
| 32 | $R^1$ = propyl | X = Br, $R^2$ = F, $R^3$ = F |
| 34 | $R^1$ = cyclopropyl | X = Br, $R^2$ = F, $R^3$ = trifluoromethyl |
| 36 | $R^1$ = cyclopropyl | X = Br, $R^2$ = F, $R^3$ = methyl |
| 38 | $R^1$ = cyclopropyl | X = Br, $R^2$ = F, $R^3$ = ethyl |
| 40 | $R^1$ = cyclopropyl | X = Br, $R^2$ = F, $R^3$ = F |
| 42 | $R^1$ = vinyl | X = Br, $R^2$ = F, $R^3$ = trifluoromethyl |
| 44 | $R^1$ = vinyl | X = Br, $R^2$ = F, $R^3$ = methyl |
| 46 | $R^1$ = vinyl | X = Br, $R^2$ = F, $R^3$ = ethyl |
| 48 | $R^1$ = vinyl | X = Br, $R^2$ = F, $R^3$ = F |
| 50 | $R^1$ = methyl | X = Br, $R^2$ = F, $R^3$ = difluoromethyl |
| 52 | $R^1$ = methyl | X = Br, $R^2$ = F, $R^3$ = fluoromethyl |
| 54 | $R^1$ = methyl | X = Br, $R^2$ = F, $R^3$ = fluoromethyl |
| 56 | $R^1$ = ethyl | X = Br, $R^2$ = F, $R^3$ = cyclopropyl |
| 58 | $R^1$ = ethyl | X = Br, $R^2$ = F, $R^3$ = fluoromethyl |
| 60 | $R^1$ = ethyl | X = Br, $R^2$ = F, $R^3$ = cyclopropyl |
| 62 | $R^1$ = propyl | X = Br, $R^2$ = F, $R^3$ = difluoromethyl |
| 64 | $R^1$ = propyl | X = Br, $R^2$ = F, $R^3$ = fluoromethyl |
| 66 | $R^1$ = propyl | X = Br, $R^2$ = F, $R^3$ = cyclopropyl |
| 68 | $R^1$ = cyclopropyl | X = Br, $R^2$ = F, $R^3$ = difluoromethyl |
| 70 | $R^1$ = cyclopropyl | X = Br, $R^2$ = F, $R^3$ = fluoromethyl |
| 72 | $R^1$ = cyclopropyl | X = Br, $R^2$ = F, $R^3$ = cyclopropyl |
| 74 | $R^1$ = vinyl | X = Br, $R^2$ = F, $R^3$ = difluoromethyl |
| 76 | $R^1$ = vinyl | X = Br, $R^2$ = F, $R^3$ = fluoromethyl |
| 78 | $R^1$ = vinyl | X = Br, $R^2$ = F, $R^3$ = cyclopropyl |

Example 5

Preparation of Compound 79

0.36 g of compound 1 was dissolved in 10 ml of acetonitrile, 0.30 g of phosphorus oxychloride was added, and the reaction mixture was heated under reflux for 20 hours. The reaction system was cooled to room temperature, and 1 g of water added and stirred for 1 hour. The solvent was removed under reduced pressure at 40° C. until the solvent was evaporated to dryness. The resulting residue was subjected to column chromatography and recrystallized from absolute ethanol to afford 0.28 g of white solid in a yield of 63% and a HPLC purity of 98.9%.

Example 6

Preparation of Compound 79

0.36 g of compound 1 was dissolved in 10 ml of acetonitrile, 0.28 g of dimethyl chlorophosphate was added, and the reaction mixture was heated under reflux for 20 hours. The reaction system was cooled to room temperature, 3 ml of methanol was added and stirred, and then 0.3 g of trimethylchlorosilane was added and stirred at room temperature for 3 hours. The solvent was evaporated to dryness, and the resulting residue was subjected to column chromatography and recrystallized from absolute ethanol to afford 0.33 g of white solid in a yield of 74% and a HPLC purity of 99.2%.

Compounds 80-156 were synthesized using a similar method to that in Example 5 and Example 6.

Example 7

In order to determine the antibacterial activity of these new oxazolidinone-based compounds, an agar dilution method was used to test the inhibitory effect on methicillin-resistant *Staphylococcus aureus* (MRSA) and vancomycin-resistant *Enterococcus* (VRE). The bacteria inhibition effect was expressed as minimum inhibitory concentration (MIC50, µg/ml) The test results are shown in the following table.

| compound | Minimum inhibitory concentration (MIC50, µg/ml) | |
|---|---|---|
| | MRSA | VRE |
| Tedizolid phosphate | 2 | 2 |
| 79 | 1.8 | 1.5 |
| 80 | 1.9 | 1.9 |
| 81 | 1.2 | 1.2 |
| 82 | 1.2 | 1.2 |
| 83 | 0.8 | 0.7 |
| 84 | 0.4 | 0.4 |
| 85 | 0.2 | 0.2 |
| 86 | 0.3 | 0.3 |
| 87 | 0.3 | 0.3 |

-continued

| compound | Minimum inhibitory concentration (MIC50, µg/ml) | |
|---|---|---|
| | MRSA | VRE |
| 88 | 0.5 | 0.5 |
| 89 | 0.4 | 0.4 |
| 90 | 2.0 | 2.0 |
| 91 | 1.3 | 1.3 |
| 92 | 0.9 | 0.9 |
| 93 | 0.7 | 0.7 |
| 94 | 1.5 | 1.5 |
| 95 | 0.3 | 0.3 |
| 96 | 0.8 | 0.8 |
| 97 | 1.1 | 1.1 |
| 98 | 1.6 | 1.5 |
| 99 | 0.2 | 0.2 |
| 100 | 0.2 | 0.3 |
| 101 | 0.4 | 0.4 |
| 102 | 0.2 | 0.2 |
| 103 | 0.7 | 0.7 |
| 104 | 0.5 | 0.5 |
| 105 | 1.4 | 1.3 |
| 106 | 1.0 | 1.2 |
| 107 | 0.8 | 0.8 |
| 108 | 0.5 | 0.4 |
| 109 | 0.2 | 0.2 |
| 110 | 0.2 | 0.2 |
| 111 | 0.3 | 0.3 |
| 112 | 0.9 | 0.9 |
| 113 | 0.2 | 0.2 |
| 114 | 0.3 | 0.3 |
| 115 | 0.5 | 0.5 |
| 116 | 0.2 | 0.3 |
| 117 | 0.4 | 0.4 |
| 118 | 0.6 | 0.6 |
| 119 | 0.7 | 0.7 |
| 120 | 0.2 | 0.2 |
| 121 | 1.1 | 1.1 |
| 122 | 1.0 | 0.9 |
| 123 | 0.3 | 0.3 |
| 124 | 0.2 | 0.2 |
| 125 | 0.3 | 0.3 |
| 126 | 0.7 | 0.7 |
| 127 | 0.6 | 0.7 |
| 128 | 0.5 | 0.5 |
| 129 | 0.5 | 0.3 |
| 130 | 0.2 | 0.2 |
| 131 | 0.2 | 0.1 |
| 132 | 0.3 | 0.3 |
| 133 | 0.3 | 0.2 |
| 134 | 0.5 | 0.5 |
| 135 | 0.4 | 0.3 |
| 136 | 0.4 | 0.2 |
| 137 | 1.5 | 1.1 |
| 138 | 1.0 | 1.0 |
| 139 | 0.8 | 0.9 |
| 140 | 0.4 | 0.4 |
| 141 | 0.3 | 0.2 |
| 142 | 0.2 | 0.2 |
| 143 | 0.3 | 0.2 |
| 144 | 0.4 | 0.4 |
| 145 | 0.6 | 0.5 |
| 150 | 0.2 | 0.2 |
| 151 | 0.8 | 0.6 |
| 152 | 0.3 | 0.2 |
| 153 | 0.2 | 0.1 |
| 154 | 0.4 | 0.3 |
| 155 | 0.9 | 0.5 |
| 156 | 0.4 | 0.4 |

As shown in the above table, when compared with tedizolid phosphate, the compounds of the present disclosure have stronger inhibitory effects on methicillin-resistant *Staphylococcus aureus* (referred to as MRSA) and vancomycin-resistant *enterococcus* (referred to as VRE). Therefore, the compounds of the present disclosure are very useful antibiotics.

What is claimed is:

1. An oxazolidinone compound of formula I and pharmaceutically acceptable salt thereof,

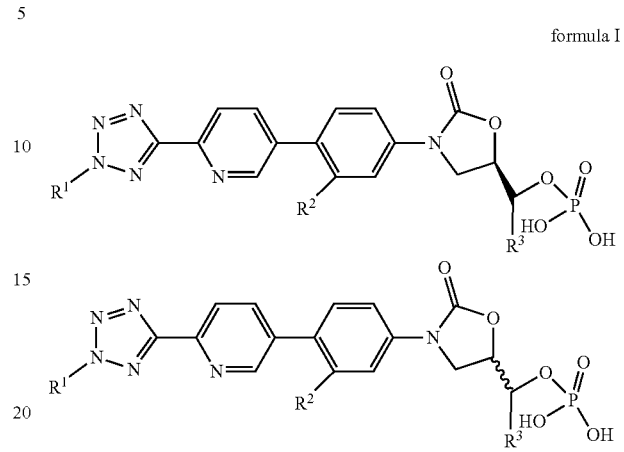

formula I wherein $R^1$ is methyl, ethyl, propyl or cyclopropyl, or vinyl; $R^2$ is F; and
wherein $R^3$ is F, $CH_3$, $C_2H_5$, $CF_3$, $CHF_2$, $CH_2F$, or cyclopropyl.

2. The compound of claim 1, wherein the compound is selected from the group consisting of:
(R)-3-(3-fluoro-4-(6-(2-ethyl-2H-tetrazol-5-yl) pyridin-3-yl) phenyl)-5-(hydroxymethyl) oxazolidin-2-one phosphate
(S)-3-(3-fluoro-4-(6-(2-ethyl-2H-tetrazol-5-yl) pyridin-3-yl) phenyl)-5-(hydroxymethyl) oxazolidin-2-one phosphate
(R)-3-(3-fluoro-4-(6-(2-propyl-2H-tetrazol-5-yl) pyridin-3-yl) phenyl)-5-(hydroxymethyl) oxazolidin-2-one phosphate
(S)-3-(3-fluoro-4-(6-(2-propyl-2H-tetrazol-5-yl) pyridin-3-yl) phenyl)-5-(hydroxymethyl) oxazolidin-2-one phosphate
(R)-3-(3-fluoro-4-(6-(2-cyclopropyl-2H-tetrazol-5-yl) pyridin-3-yl) phenyl)-5-(hydroxylmethyl) oxazolidin-2-one phosphate
(S)-3-(3-fluoro-4-(6-(2-cyclopropyl-2H-tetrazol-5-yl) pyridin-3-yl) phenyl)-5-(hydroxylmethyl) oxazolidin-2-one phosphate
(R)-3-(3-fluoro-4-(6-(2-vinyl-2H-tetrazol-5-yl) pyridin-3-yl) phenyl)-5-(hydroxymethyl) oxazolidin-2-one phosphate
(S)-3-(3-fluoro-4-(6-(2-vinyl-2H-tetrazol-5-yl) pyridin-3-yl) phenyl)-5-(hydroxymethyl) oxazolidin-2-one phosphate
(R)-3-(3-fluoro-4-(6-(2-methyl-2H-tetrazol-5-yl) pyridin-3-yl) phenyl)-5-(1-hydroxyethyl) oxazolidin-2-one phosphate
(S)-3-(3-fluoro-4-(6-(2-methyl-2H-tetrazol-5-yl) pyridin-3-yl) phenyl)-5-(1-hydroxyethyl) oxazolidin-2-one phosphate
(R)-3-(3-fluoro-4-(6-(2-methyl-2H-tetrazol-5-yl) pyridin-3-yl) phenyl)-5-(1-hydroxypropyl) oxazolidin-2-one phosphate
(S)-3-(3-fluoro-4-(6-(2-methyl-2H-tetrazol-5-yl) pyridin-3-yl) phenyl)-5-(1-hydroxypropyl) oxazolidin-2-one phosphate
(R)-3-(3-fluoro-4-(6-(2-methyl-2H-tetrazol-5-yl) pyridin-3-yl) phenyl)-5-(hydroxyfluoromethyl) oxazolidin-2-one phosphate (S)-3-(3-fluoro-4-(6-(2-methyl-2H-tetrazol-5-yl) pyridin-3-yl) phenyl)-5-(hydroxyfluoromethyl) oxazolidin-2-one phosphate (R)-3-(3-fluoro-4-(6-(2-methyl-2H-tetrazol-5-yl) pyridin-3-yl) phenyl)-5-(1-hydroxy-2,2,2-trifluoroethyl) oxazolidin-2-one phosphate (S)-3-(3-fluoro-4-(6-(2-methyl-2H-tetrazol-5-yl) pyridin-3-yl) phenyl)-5-(1-hydroxy-2,2,2-trifluoro-ethyl) oxazolidin-2-one phosphate (R)-3-(3-fluoro-4-(6-(2-ethyl-2H-tetrazol-5-yl) pyridin-3-yl) phenyl)-5-(1-hydroxy-2,2,2-trifluoro-ethyl) oxazolidin-2-one phosphate (S)-3-(3-fluoro-4-(6-(2-ethyl-2H-tetrazol-5-yl) pyridin-3-yl) phenyl)-5-(1-hydroxy-2,2,2-trifluoro-ethyl) oxazolidin-2-one phosphate (R)-3-(3-fluoro-4-(6-(2-ethyl-2H-tetrazol-5-yl) pyridin-3-yl) phenyl)-5-(1-hydroxyethyl) oxazolidin-2-one phosphate (S)-3-(3-fluoro-4-(6-(2-ethyl-2H-tetrazol-5-yl) pyridin-3-yl) phenyl)-5-(1-hydroxyethyl) oxazolidin-2-one phosphate (R)-3-(3-fluoro-4-(6-(2-ethyl-2H-tetrazol-5-yl) pyridin-3-yl) phenyl)-5-(1-hydroxypropyl) oxazolidin-2-one phosphate (S)-3-(3-fluoro-4-(6-(2-ethyl-2H-tetrazol-5-yl) pyridin-3-yl) phenyl)-5-(1-hydroxypropyl) oxazolidin-2-one phosphate (R)-3-(3-fluoro-4-(6-(2-ethyl-2H-tetrazol-5-yl) pyridin-3-yl) phenyl)-5-(hydroxyfluoromethyl) oxazolidin-2-one phosphate (S)-3-(3-fluoro-4-(6-(2-ethyl-2H-tetrazol-5-yl) pyridin-3-yl) phenyl)-5-(hydroxyfluoromethyl) oxazolidin-2-one phosphate (R)-3-(3-fluoro-4-(6-(2-propyl-2H-tetrazol-5-yl) pyridin-3-yl) phenyl)-5-(1-hydroxy-2,2,2-trifluoro-ethyl) oxazolidin-2-one phosphate (S)-3-(3-fluoro-4-(6-(2-propyl-2H-tetrazol-5-yl) pyridin-3-yl) phenyl)-5-(1-hydroxy-2,2,2-trifluoro-ethyl) oxazolidin-2-one phosphate (R)-3-(3-fluoro-4-(6-(2-propyl-2H-tetrazol-5-yl) pyridin-3-yl) phenyl)-5-(1-hydroxyethyl) oxazolidin-2-one phosphate (S)-3-(3-fluoro-4-(6-(2-propyl-2H-tetrazol-5-yl) pyridin-3-yl) phenyl)-5-(1-hydroxyethyl) oxazolidin-2-one phosphate (R)-3-(3-fluoro-4-(6-(2-propyl-2H-tetrazol-5-yl) pyridin-3-yl) phenyl)-5-(1-hydroxypropyl) oxazolidin-2-one phosphate (S)-3-(3-fluoro-4-(6-(2-propyl-2H-tetrazol-5-yl) pyridin-3-yl) phenyl)-5-(1-hydroxypropyl) oxazolidin-2-one phosphate (R)-3-(3-fluoro-4-(6-(2-propyl-2H-tetrazol-5-yl) pyridin-3-yl) phenyl)-5-(hydroxyfluoro-methyl) oxazolidin-2-one phosphate (S)-3-(3-fluoro-4-(6-(2-propyl-2H-tetrazol-5-yl) pyridin-3-yl) phenyl)-5-(hydroxyfluoromethyl) oxazolidin-2-one phosphate (R)-3-(3-fluoro-4-(6-(2-cyclopropyl-2H-tetrazol-5-yl) pyridin-3-yl) phenyl)-5-(1-hydroxy-2-tri-fluoroethyl) oxazolidin-2-one phosphate (S)-3-(3-fluoro-4-(6-(2-cyclopropyl-2H-tetrazol-5-yl) pyridin-3-yl) phenyl)-5-(1-hydroxy-2,2,2-trifluoro-ethyl) oxazolidin-2-one phosphate (R)-3-(3-fluoro-4-(6-(2-cyclopropyl-2H-tetrazol-5-yl) pyridin-3-yl) phenyl)-5-(1-hydroxyethyl) oxazolidin-2-one phosphate (S)-3-(3-fluoro-4-(6-(2-cyclopropyl-2H-tetrazol-5-yl) pyridin-3-yl) phenyl)-5-(1-hydroxyethyl) oxazolidin-2-one phosphate (R)-3-(3-fluoro-4-(6-(2-cyclopropyl-2H-tetrazol-5-yl) pyridin-3-yl) phenyl)-5-(1-hydroxypropyl) oxazolidin-2-one phosphate (S)-3-(3-fluoro-4-(6-(2-cyclopropyl-2H-tetrazol-5-yl) pyridin-3-yl) phenyl)-5-(1-hydroxypropyl) oxazolidin-2-one phosphate (R)-3-(3-fluoro-4-(6-(2-cyclopropyl-2H-tetrazol-5-yl) pyridin-3-yl) phenyl)-5-(hydroxyfluoro-methyl) oxazolidin-2-one phosphate (S)-3-(3-fluoro-4-(6-(2-cyclopropyl-2H-tetrazol-5-yl) pyridin-3-yl) phenyl)-5-(hydroxyfluoromethyl) oxazolidin-2-one phosphate (R)-3-(3-fluoro-4-(6-(2-vinyl-2H-tetrazol-5-yl) pyridin-3-yl) phenyl)-5-(1-hydroxy-2,2,2-trifluoroethyl) oxazolidin-2-one phosphate (S)-3-(3-fluoro-4-(6-(2-vinyl-2H-tetrazol-5-yl) pyridin-3-yl) phenyl)-5-(1-hydroxy-2,2,2-trifluoroethyl) oxazolidin-2-one phosphate (R)-3-(3-fluoro-4-(6-(2-vinyl-2H-tetrazol-5-yl) pyridin-3-yl) phenyl)-5-(1-hydroxyethyl) oxazolidin-2-one phosphate (S)-3-(3-fluoro-4-(6-(2-vinyl-2H-tetrazol-5-yl) pyridin-3-yl) phenyl)-5-(1-hydroxyethyl) oxazolidin-2-one phosphate (R)-3-(3-fluoro-4-(6-(2-vinyl-2H-tetrazol-5-yl) pyridin-3-yl) phenyl)-5-(1-hydroxypropyl) oxazolidin-2-one phosphate (S)-3-(3-fluoro-4-(6-(2-vinyl-2H-tetrazol-5-yl) pyridin-3-yl) phenyl)-5-(1-hydroxypropyl) oxazolidin-2-one phosphate (R)-3-(3-fluoro-4-(6-(2-vinyl-2H-tetrazol-5-yl) pyridin-3-yl) phenyl)-5-(hydroxyfluoromethyl) oxazolidin-2-one phosphate (S)-3-(3-fluoro-4-(6-(2-vinyl-2H-tetrazol-5-yl) pyridin-3-yl) phenyl)-5-(hydroxyfluoromethyl) oxazolidin-2-one phosphate (R)-3-(3-fluoro-4-(6-(2-methyl-2H-tetrazol-5-yl) pyridin-3-yl) phenyl)-5-(1-hydroxy-2-difluoroethyl) oxazolidin-2-one phosphate (S)-3-(3-fluoro-4-(6-(2-methyl-2H-tetrazol-5-yl) pyridin-3-yl) phenyl)-5-(1-hydroxy-2-difluoroethyl) oxazolidin-2-one phosphate (R)-3-(3-fluoro-4-(6-(2-methyl-2H-tetrazol-5-yl) pyridin-3-yl) phenyl)-5-(1-hydroxy-2-fluoro-ethyl) oxazolidin-2-one phosphate (S)-3-(3-fluoro-4-(6-(2-methyl-2H-tetrazol-5-yl) pyridin-3-yl) phenyl)-5-(1-hydroxy-2-fluoro-ethyl) oxazolidin-2-one phosphate (R)-3-(3-fluoro-4-(6-(2-methyl-2H-tetrazol-5-yl) pyridin-3-yl) phenyl)-5-(1-hydroxy-1-cyclo-propylmethyl) oxazolidin-2-one phosphate (S)-3-(3-fluoro-4-(6-(2-methyl-2H-tetrazol-5-yl) pyridin-3-yl) phenyl)-5-(1-hydroxy-1-cyclo-propylmethyl) oxazolidin-2-one phosphate (R)-3-(3-fluoro-4-(6-(2-ethyl-2H-tetrazol-5-yl) pyridin-3-yl) phenyl)-5-(1-hydroxy-2,2-difluoro-ethyl) oxazolidin-2-one phosphate (S)-3-(3-fluoro-4-(6-(2-ethyl-2H-tetrazol-5-yl) pyridin-3-yl) phenyl)-5-(1-hydroxy-2,2-difluoro-ethyl) oxazolidin-2-one phosphate (R)-3-(3-fluoro-4-(6-(2-ethyl-2H-tetrazol-5-yl) pyridin-3-yl) phenyl)-5-(1-hydroxy-2-fluoroe-thyl) oxazolidin-2-one phosphate (S)-3-(3-fluoro-4-(6-(2-ethyl-2H-tetrazol-5-yl) pyridin-3-yl) phenyl)-5-(1-hydroxy-2-fluoro-ethyl) oxazolidin-2-one phosphate (R)-3-(3-fluoro-4-(6-(2-ethyl-2H-tetrazol-5-yl) pyridin-3-yl) phenyl)-5-(1-hydroxy-1-cyclo-propylmethyl) oxazolidin-2-one phosphate (S)-3-(3-fluoro-4-(6-(2-ethyl-2H-tetrazol-5-yl) pyridin-3-yl) phenyl)-5-(1-hydroxy-1-cyclo-propylmethyl) oxazolidin-2-one phosphate (R)-3-(3-fluoro-4-(6-(2-propyl-2H-tetrazol-5-yl) pyridin-3-yl) phenyl)-5-(1-hydroxy-2,2-difluoro-ethyl) oxazolidin-2-one phosphate (S)-3-(3-fluoro-4-(6-(2-propyl-2H-tetrazol-5-yl) pyridin-3-yl) phenyl)-5-(1-hydroxy-2,2-difluoro-ethyl) oxazolidin-2-one phosphate (R)-3-(3-fluoro-4-(6-(2-propyl-2H-tetrazol-5-yl) pyridin-3-yl) phenyl)-5-(1-hydroxy-2-fluoro-ethyl) oxazolidin-2-one phosphate (S)-3-(3-fluoro-4-(6-(2-propyl-2H-tetrazol-5-yl) pyridin-3-yl) phenyl)-5-(1-hydroxy-2-fluoro-ethyl) oxazolidin-2-one phosphate (R)-3-(3-fluoro-4-(6-(2-propyl-2H-tetrazol-5-yl) pyridin-3-yl) phenyl)-5-(1-hydroxy-1-cyclo-propylmethyl) oxazolidin-2-one phosphate (S)-3-(3-fluoro-4-(6-(2-propyl-2H-tetrazol-5-yl) pyridin-3-yl) phenyl)-5-(1-hydroxy-1-cyclo-propylmethyl) oxazolidin-2-one phosphate (R)-3-(3-fluoro-4-(6-(2-cyclopropyl-2H-tetrazol-5-yl) pyridin-3-yl) phenyl)-5-(1-hydroxy-2,2-difluoroethyl) oxazolidin-2-one phosphate (S)-3-(3-fluoro-4-(6-(2-cyclopropyl-2H-tetrazol-5-yl) pyridin-3-yl) phenyl)-5-(1-hydroxy-2,2-difluoroethyl) oxazolidin-2-one phosphate (R)-3-(3-fluoro-4-(6-(2-cyclopropyl-2H-tetrazol-5-yl) pyridin-3-yl) phenyl)-5-(1-hydroxy-2-fluoroethyl) oxazolidin-2-one phosphate (S)-3-(3-fluoro-4-(6-(2-cyclopropyl-2H-tetrazol-5-yl) pyridin-3-yl) phenyl)-5-(1-hydroxy-2-fluoroethyl) oxazolidin-2-one phosphate (R)-3-(3-fluoro-4-(6-(2-cyclopropyl-2H-tetrazol-5-yl) pyridin-3-yl) phenyl)-5-(1-hydroxy-1-cyclopropylmethyl) oxazolidin-2-one phosphate (S)-3-(3-fluoro-4-(6-(2-cyclopropyl-2H-tetrazol-5-yl) pyridin-3-yl) phenyl)-5-(1-hydroxy-1-cyclopropylmethyl) oxazolidin-2-one phosphate (R)-3-(3-fluoro-4-(6-(2-vinyl-2H-tetrazol-5-yl) pyridin-3-yl) phenyl)-5-(1-hydroxy-2-difluoro-ethyl) oxazolidin-2-one phosphate (S)-3-(3-fluoro-4-(6-(2-vinyl-2H-tetrazol-5-yl) pyridin-3-yl) phenyl)-5-(1-hydroxy-2,2-difluoro-ethyl) oxazolidin-2-one phosphate (R)-3-(3-fluoro-4-(6-(2-vinyl-2H-tetrazol-5-yl) pyridin-3-yl) phenyl)-5-(1-hydroxy-2,2-fluoro-ethyl) oxazolidin-2-one phosphate (S)-3-(3-fluoro-4-(6-(2-vinyl-2H-tetrazol-5-yl) pyridin-3-yl) phenyl)-5-(1-hydroxy-2-fluoro-ethyl) oxazolidin-2-one phosphate (R)-3-(3-fluoro-4-(6-(2-vinyl-2H-tetrazol-5-yl) pyridin-3-yl) phenyl)-5-(1-hydroxy-1-cyclo-propylmethyl) oxazolidin-2-one phosphate (S)-3-(3-fluoro-4-(6-(2-vinyl-2H-tetrazol-5-yl) pyridin-3-yl) phenyl)-5-(1-hydroxy-1-cyclo-propylmethyl) oxazolidin-2-one phosphate.

3. A method for preparing the compound of formula I according to claim 1, comprising steps of reacting a compound having a structure of formula II with a halogenated phosphate ester, and reacting a resulting product with trimethylhalosilane

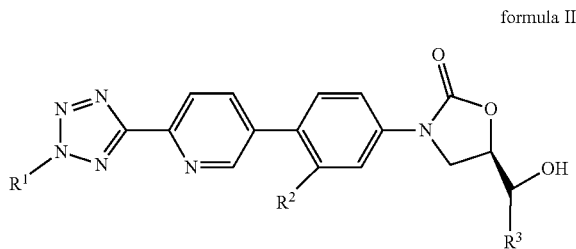

formula II wherein $R^1$ is methyl, ethyl, propyl, cyclopropyl, or vinyl; $R^2$ is F; $R^3$ is F, $CH_3$, $C_2H_5$, $CF_3$, $CHF_2$, $CH_2F$, or cyclopropyl.

4. A method for preparing the compound of formula I according to claim 1, comprising steps of reacting a compound having a structure of formula II with phosphorus oxychloride, and hydrolyzing a resulting product

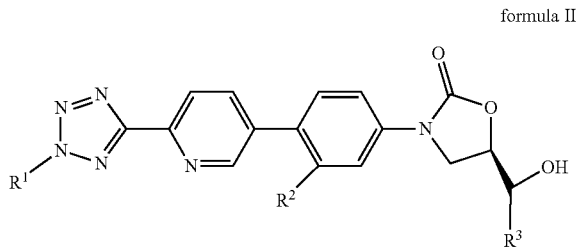

formula II wherein $R^1$ is methyl, ethyl, propyl, cyclopropyl, or vinyl; $R^2$ is F; $R^3$ is F, $CH_3$, $C_2H_5$, $CF_3$, $CHF_2$, $CH_2F$, or cyclopropyl.

5. The method according to claim 3, wherein the halogenated phosphate ester is selected from the group consisting of dimethyl chlorophosphate, diethyl chlorophosphate, dibenzyl chlorophosphate, dimethyl bromophosphate, diethyl bromophosphate ester, and dibenzyl bromophosphate.

6. The method according to claim 3, wherein the trimethylhalosilane is selected from the group consisting of trimethylbromosilane and trimethylchlorosilane.

7. The method according to claim 3, wherein the compound having the structure of formula II is selected from the group consisting of the following compounds:

(R)-3-(3-fluoro-4-(6-(2-ethyl-2H-tetrazol-5-yl) pyridin-3-yl) phenyl)-5-(hydroxymethyl) oxazolidin-2-one (S)-3-(3-fluoro-4-(6-(2-ethyl-2H-tetrazol-5-yl) pyridin-3-yl) phenyl)-5-(hydroxylmethyl) oxazolidin-2-one (R)-3-(3-fluoro-4-(6-(2-propyl-2H-tetrazol-5-yl) pyridin-3-yl) phenyl)-5-(hydroxymethyl) oxazolidin-2-one (S)-3-(3-fluoro-4-(6-(2-propyl-2H-tetrazol-5-yl) pyridine-3-yl) phenyl)-5-(hydroxymethyl) oxazolidin-2-one (R)-3-(3-fluoro-4-(6-(2-cyclopropyl-2H-tetrazole-5)-yl) pyridin-3-yl) phenyl)-5-(hydroxymethyl) oxazolidin-2-one (S)-3-(3-fluoro-4-(6-(2-cyclopropyl-2H-tetrazol-5-yl) pyridin-3-yl) phenyl)-5-(hydroxymethyl) oxane oxazolidin-2-one (R)-3-(3-fluoro-4-(6-(2-vinyl-2H-tetrazol-5-yl) pyridin-3-yl) phenyl)-5-(hydroxymethyl) oxazolidin-2-one (S)-3-(3-fluoro-4-(6-(2-vinyl-2H-tetrazol-5-yl) pyridin-3-yl) phenyl)-5-(hydroxymethyl) oxazolidin-2-one (R)-3-(3-fluoro-4-(6-(2-methyl-2H-tetrazol-5-yl) pyridin-3-yl) phenyl)-5-(1-hydroxyethyl) oxazolidin-2-one (S)-3-(3-fluoro-4-(6-(2-methyl-2H-tetrazol-5-yl) pyridin-3-yl) phenyl)-5-(1-hydroxyethyl) oxazolidin-2-one (R)-3-(3-fluoro-4-(6-(2-methyl-2H-tetrazol-5-yl) pyridin-3-yl) phenyl)-5-(1-hydroxypropyl) oxazolidin-2-one (S)-3-(3-fluoro-4-(6-(2-methyl-2H-tetrazol-5-yl) pyridin-3-yl) phenyl)-5-(1-hydroxypropyl) oxazolidin-2-one (R)-3-(3-fluoro-4-(6-(2-methyl-2H-tetrazol-5-yl) pyridin-3-yl) phenyl)-5-(hydroxyfluoromethyl) oxazolidin-2-one (S)-3-(3-fluoro-4-(6-(2-methyl-2H-tetrazol-5-yl) pyridin-3-yl) phenyl)-5-(hydroxyfluoromethyl) oxazolidin-2-one (R)-3-(3-fluoro-4-(6-(2-methyl-2H-tetrazol-5-yl) pyridin-3-yl) phenyl)-5-(1-hydroxy-2,2,2-trifluoroethyl) oxazolidin-2-one (S)-3-(3-fluoro-4-(6-(2-methyl-2H-tetrazol-5-yl) pyridin-3-yl) phenyl)-5-(1-hydroxy-2,2,2-trifluoroethyl) oxazolidin-2-one (R)-3-(3-fluoro-4-(6-(2-ethyl-2H-tetrazol-5-yl) pyridin-3-yl) phenyl)-5-(1-hydroxy-2,2,2-trifluoroethyl) oxazolidin-2-one (S)-3-(3-fluoro-4-(6-(2-ethyl-2H-tetrazol-5-yl) pyridin-3-yl) phenyl)-5-(1-hydroxy-2,2,2-trifluoroethyl) oxazolidin-2-one (R)-3-(3-fluoro-4-(6-(2-ethyl-2H-tetrazol-5-yl) pyridin-3-yl) phenyl)-5-(1-hydroxyethyl) oxazolidin-2-one (S)-3-(3-fluoro-4-(6-(2-ethyl-2H-tetrazol-5-yl) pyridin-3-yl) phenyl)-5-(1-hydroxyethyl) oxazolidin-2-one (R)-3-(3-fluoro-4-(6-(2-ethyl-2H-tetrazol-5-yl) pyridin-3-yl) phenyl)-5-(1-hydroxypropyl) oxazolidin-2-one (S)-3-(3-fluoro-4-(6-(2-ethyl-2H-tetrazol-5-yl) pyridin-3-yl) phenyl)-5-(1-hydroxypropyl) oxazolidin-2-one (R)-3-(3-fluoro-4-(6-(2-ethyl-2H-tetrazol-5-yl) pyridin-3-yl) phenyl)-5-(hydroxyfluoromethyl) oxazolidin-2-one (S)-3-(3-fluoro-4-(6-(2-ethyl-2H-tetrazol-5-yl) pyridin-3-yl) phenyl)-5-(hydroxyfluoromethyl) oxazolidin-2-one (R)-3-(3-fluoro-4-(6-(2-propyl-2H-tetrazol-5-yl) pyridin-3-yl) phenyl)-5-(1-hydroxy-2,2,2-trifluoroethyl) oxazolidin-2-one (S)-3-(3-fluoro-4-(6-(2-propyl-2H-tetrazol-5-yl) pyridin-3-yl) phenyl)-5-(1-hydroxy-2,2,2-trifluoroethyl) oxazolidin-2-one (R)-3-(3-fluoro-4-(6-(2-propyl-2H-tetrazol-5-yl) pyridin-3-yl) phenyl)-5-(1-hydroxyethyl) oxazolidin-2-one (S)-3-(3-fluoro-4-(6-(2-propyl-2H-tetrazol-5-yl) pyridin-3-yl) phenyl)-5-(1-hydroxyethyl) oxazolidin-2-one (R)-3-(3-fluoro-4-(6-(2-propyl-2H-tetrazol-5-yl) pyridin-3-yl) phenyl)-5-(1-hydroxypropyl) oxazolidin-2-one (S)-3-(3-fluoro-4-(6-(2-propyl-2H-tetrazol-5-yl) pyridin-3-yl) phenyl)-5-(1-hydroxypropyl) oxazolidin-2-one (R)-3-(3-fluoro-4-(6-(2-propyl-2H-tetrazol-5-yl) pyridin-3-yl) phenyl)-5-(hydroxyfluoromethyl) oxazolidin-2-one (S)-3-(3-fluoro-4-(6-(2-propyl-2H-tetrazol-5-yl) pyridin-3-yl) phenyl)-5-(hydroxyfluoromethyl) oxazolidin-2-one (R)-3-(3-fluoro-4-(6-(2-cyclopropyl-2H-tetrazol-5-yl) pyridin-3-yl) phenyl)-5-(1-hydroxy-2,2,2-trifluoroethyl) oxazolidin-2-one (S)-3-(3-fluoro-4-(6-(2-cyclopropyl-2H-tetrazol-5-yl) pyridin-3-yl) phenyl)-5-(1-hydroxy-2,2,2-trifluoroethyl) oxazolidin-2-one (R)-3-(3-fluoro-4-(6-(2-cyclopropyl-2H-tetrazol-5-yl) pyridin-3-yl) phenyl)-5-(1-hydroxyethyl) oxazolidin-2-one (S)-3-(3-fluoro-4-(6-(2-cyclopropyl-2H-tetrazol-5-yl) pyridin-3-yl) phenyl)-5-(1-hydroxyethyl) oxazolidin-2-one (R)-3-(3-fluoro-4-(6-(2-cyclopropyl-2H-tetrazol-5-yl) pyridin-3-yl) phenyl)-5-(1-hydroxypropyl)) oxazolidin-2-one (S)-3-(3-fluoro-4-(6-(2-cyclopropyl-2H-tetrazol-5-yl) pyridin-3-yl) phenyl)-5-(1-hydroxypropyl)) oxazolidin-2-one (R)-3-(3-fluoro-4-(6-(2-cyclopropyl-2H-tetrazol-5-yl) pyridin-3-yl) phenyl)-5-(hydroxyfluoromethyl)) oxazolidin-2-one (S)-3-(3-fluoro-4-(6-(2-cyclopropyl-2H-tetrazol-5-yl) pyridin-3-yl) phenyl)-5-(hydroxyfluoromethyl)) oxazolidin-2-one (R)-3-(3-fluoro-4-(6-(2-vinyl-2H-tetrazol-5-yl) pyridin-3-yl) phenyl)-5-(1-hydroxy-2,2,2-trifluoroethyl) oxazolidin-2-one (S)-3-(3-fluoro-4-(6-(2-vinyl-2H-tetrazol-5-yl) pyridin-3-yl) phenyl)-5-(1-hydroxy-2,2,2-trifluoroethyl) oxazolidin-2-one (R)-3-(3-fluoro-4-(6-(2-vinyl-2H-tetrazol-5-yl) pyridin-3-yl) phenyl)-5-(1-hydroxyethyl) oxazolidin-2-one (S)-3-(3-fluoro-4-(6-(2-vinyl-2H-tetrazol-5-yl) pyridin-3-yl) phenyl)-5-(1-hydroxyethyl) oxazolidin-2-one (R)-3-(3-fluoro-4-(6-(2-vinyl-2H-tetrazol-5-yl) pyridin-3-yl) phenyl)-5-(1-hydroxypropyl) oxazolidin-2-one (S)-3-(3-fluoro-4-(6-(2-vinyl-2H-tetrazol-5-yl) pyridin-3-yl) phenyl)-5-(1-hydroxypropyl) oxazolidin-2-one (R)-3-(3-fluoro-4-(6-(2-vinyl-2H-tetrazol-5-yl) pyridin-3-yl) phenyl)-5-(hydroxyfluoromethyl) oxazolidin-2-one (S)-3-(3-fluoro-4-(6-(2-vinyl-2H-tetrazol-5-yl) pyridin-3-yl) phenyl)-5-(hydroxyfluoromethyl) oxazolidin-2-one (R)-3-(3-fluoro-4-(6-(2-methyl-2H-tetrazol-5-yl) pyridin-3-yl) phenyl)-5-(1-hydroxy-2,2-difluoroethyl) oxazolidin-2-one (S)-3-(3-fluoro-4-(6-(2-methyl-2H-tetrazol-5-yl) pyridin-3-yl) phenyl)-5-(1-hydroxy-2,2-difluoroethyl) oxazolidin-2-one (R)-3-(3-fluoro-4-(6-(2-methyl-2H-tetrazol-5-yl) pyridin-3-yl) phenyl)-5-(1-hydroxy-2-fluoroethyl) oxazolidin-2-one (referred to as compound 51)

(S)-3-(3-fluoro-4-(6-(2-methyl-2H-tetrazol-5-yl) pyridin-3-yl) phenyl)-5-(1-hydroxy-2-fluoroethyl) oxazolidin-2-one (R)-3-(3-fluoro-4-(6-(2-methyl-2H-tetrazol-5-yl) pyridin-3-yl) phenyl)-5-(1-hydroxy-1-cyclopropylmethyl) oxazolidin-2-one (S)-3-(3-fluoro-4-(6-(2-methyl-2H-tetrazol-5-yl) pyridin-3-yl) phenyl)-5-(1-hydroxy-1-cyclopropylmethyl) oxazolidin-2-one (R)-3-(3-fluoro-4-(6-(2-ethyl-2H-tetrazol-5-yl) pyridin-3-yl) phenyl)-5-(1-hydroxy-2,2-difluoroethyl) oxazolidin-2-one (S)-3-(3-fluoro-4-(6-(2-ethyl-2H-tetrazol-5-yl) pyridin-3-yl) phenyl)-5-(1-hydroxy-2,2-difluoroethyl) oxazolidin-2-one (R)-3-(3-fluoro-4-(6-(2-ethyl-2H-tetrazol-5-yl) pyridin-3-yl) phenyl)-5-(1-hydroxy-2-fluoroethyl) oxazolidin-2-one (S)-3-(3-fluoro-4-(6-(2-ethyl-2H-tetrazol-5-yl) pyridin-3-yl) phenyl)-5-(1-hydroxy-2-fluoroethyl) oxazolidin-2-one (R)-3-(3-fluoro-4-(6-(2-ethyl-2H-tetrazol-5-yl) pyridin-3-yl) phenyl)-5-(1-hydroxy-1-cyclopropylmethyl) oxazolidin-2-one (S)-3-(3-fluoro-4-(6-(2-ethyl-2H-tetrazol-5-yl) pyridin-3-yl) phenyl)-5-(1-hydroxy-1-cyclopropylmethyl) oxazolidin-2-one (R)-3-(3-fluoro-4-(6-(2-propyl-2H-tetrazol-5-yl) pyridin-3-yl) phenyl)-5-(1-hydroxy-2-difluoroethyl) oxazolidin-2-one (S)-3-(3-fluoro-4-(6-(2-propyl-2H-tetrazol-5-yl) pyridin-3-yl) phenyl)-5-(1-hydroxy-2,2-difluoroethyl) oxazolidin-2-one (R)-3-(3-fluoro-4-(6-(2-propyl-2H-tetrazol-5-yl) pyridin-3-yl) phenyl)-5-(1-hydroxy-2-fluoroethyl) oxazolidin-2-one (S)-3-(3-fluoro-4-(6-(2-propyl-2H-tetrazol-5-yl) pyridin-3-yl) phenyl)-5-(1-hydroxy-2-fluoroethyl) oxazolidin-2-one (R)-3-(3-fluoro-4-(6-(2-propyl-2H-tetrazol-5-yl) pyridin-3-yl) phenyl)-5-(1-hydroxy-1-cyclopropylmethyl) oxazolidin-2-one (S)-3-(3-fluoro-4-(6-(2-propyl-2H-tetrazol-5-yl) pyridin-3-yl) phenyl)-5-(1-hydroxy-1-cyclopropylmethyl) oxazolidin-2-one (R)-3-(3-fluoro-4-(6-(2-cyclopropyl-2H-tetrazol-5-yl) pyridin-3-yl) phenyl)-5-(1-hydroxy-2,2-difluoroethyl) oxazolidin-2-one (S)-3-(3-fluoro-4-(6-(2-cyclopropyl-2H-tetrazol-5-yl) pyridin-3-yl) phenyl)-5-(1-hydroxy-2,2-difluoroethyl) oxazolidin-2-one (R)-3-(3-fluoro-4-(6-(2-cyclopropyl-2H-tetrazol-5-yl) pyridin-3-yl) phenyl)-5-(1-hydroxy-2-fluoroethyl) oxazolidin-2-one (S)-3-(3-fluoro-4-(6-(2-cyclopropyl-2H-tetrazol-5-yl) pyridin-3-yl) phenyl)-5-(1-hydroxy-2-fluoroethyl) oxazolidin-2-one (R)-3-(3-fluoro-4-(6-(2-cyclopropyl-2H-tetrazol-5-yl) pyridin-3-yl) phenyl)-5-(1-hydroxy-1-cyclopropylmethyl) oxazolidin-2-one (S)-3-(3-fluoro-4-(6-(2-cyclopropyl-2H-tetrazol-5-yl) pyridin-3-yl) phenyl)-5-(1-hydroxy-1-cyclopropylmethyl) oxazolidin-2-one (R)-3-(3-fluoro-4-(6-(2-vinyl-2H-tetrazol-5-yl) pyridin-3-yl) phenyl)-5-(1-hydroxy-2,2-difluoroethyl) oxazolidin-2-one (S)-3-(3-fluoro-4-(6-(2-vinyl-2H-tetrazol-5-yl) pyridin-3-yl) phenyl)-5-(1-hydroxy-2,2-difluoroethyl) oxazolidin-2-one (R)-3-(3-fluoro-4-(6-(2-vinyl-2H-tetrazol-5-yl) pyridin-3-yl) phenyl)-5-(1-hydroxy-2-fluoroethyl) oxazolidin-2-one (S)-3-(3-fluoro-4-(6-(2-vinyl-2H-tetrazol-5-yl) pyridin-3-yl) phenyl)-5-(1-hydroxy-2-fluoroethyl) oxazolidin-2-one (R)-3-(3-fluoro-4-(6-(2-vinyl-2H-tetrazol-5-yl) pyridin-3-yl) phenyl)-5-(1-hydroxy-1-cyclopropylmethyl) oxazolidin-2-one (S)-3-(3-fluoro-4-(6-(2-vinyl-2H-tetrazol-5-yl) pyridin-3-yl) phenyl)-5-(1-hydroxy-1-cyclopropylmethyl) oxazolidin-2-one.

8. A method for treating a bacterial infection disease, comprising a step of administering a compound of formula I according to claim 1 and salts thereof to a patient in need thereof

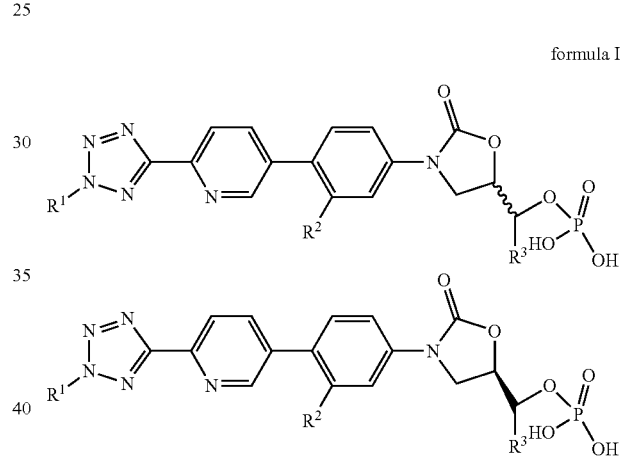

formula I

* * * * *